(12) United States Patent
Vanotti et al.

(10) Patent No.: US 7,618,982 B2
(45) Date of Patent: Nov. 17, 2009

(54) HETEROARYLPYRROLOPYRIDINONES ACTIVE AS KINASE INHIBITORS

(75) Inventors: Ermes Vanotti, Milan (IT); Barbara Forte, Milan (IT); Katia Martina, Novara (IT); Maria Menichincheri, Milan (IT); Alessandra Cirla, Varese (IT); Paolo Orsini, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 488 days.

(21) Appl. No.: 11/311,386

(22) Filed: Dec. 19, 2005

(65) Prior Publication Data
US 2007/0142415 A1 Jun. 21, 2007

(51) Int. Cl.
*C07D 471/02* (2006.01)
(52) U.S. Cl. .................................. 514/300; 546/113
(58) Field of Classification Search ............... 546/113; 514/300
See application file for complete search history.

(56) References Cited

U.S. PATENT DOCUMENTS 6,417,202 B1 * 7/2002 Kawai et al. ............... 514/333

FOREIGN PATENT DOCUMENTS

| WO | WO 00/69846 | 11/2000 |
|---|---|---|
| WO | WO 01/98299 A1 | 12/2001 |
| WO | WO 02/12242 A2 | 2/2002 |
| WO | WO 03/014090 A1 | 2/2003 |
| WO | WO 03/027114 A1 | 4/2003 |
| WO | WO 03/028720 A1 | 4/2003 |
| WO | WO 2004/058762 A1 | 7/2004 |
| WO | WO 2005/013986 A1 | 2/2005 |
| WO | WO 2005/014572 A1 | 2/2005 |
| WO | WO 2005/058762 A1 | 6/2005 |

OTHER PUBLICATIONS

Lipinski C.A. et al., "2-Amino-and 2-Guanidino-4-Thiazolylpyrimidines", *J. Heterocyclic Chem.*, 22:1723-1726 (1985).
Cohen P., "The Development and Therapeutic Potential of Protein Kinase Inhibitors", *Current Opinion in Chemical Biology*, 3:459-465 (1999).
Montagnoli A. et al., "Drf1, a Novel Regulatory Subunit for Human Cdc7 Kinase", *The EMBO Journal*, 21(12):3171-3181 (2002).
Montagnoli A. et al., "Cdc7 Inhibition Reveals a p53-Dependent Replication Checkpoint That Is Defective in Cancer Cells", *Cancer Research*, 64:7110-7116 (2004).

* cited by examiner

*Primary Examiner*—Janet L. Andres
*Assistant Examiner*—Raymond Covington
(74) *Attorney, Agent, or Firm*—Scully, Scott, Murphy & Presser, P.C.

(57) ABSTRACT

Compounds represented by formula (I)

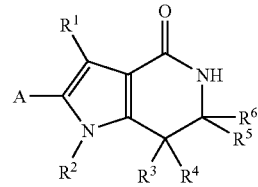

wherein A, $R^1$, $R^2$, $R^3$, $R^4$, $R^5$ and $R^6$ are as defined in the specification or a pharmaceutically acceptable salt or solvate thereof,
compositions thereof, and methods of use thereof.

9 Claims, No Drawings

HETEROARYLPYRROLOPYRIDINONES ACTIVE AS KINASE INHIBITORS

FIELD OF THE INVENTION

The present invention relates to heteroarylpyrrolopyridinones, to pharmaceutical compositions comprising them and to their use as therapeutic agents, particularly in the treatment of cancer and cell proliferation disorders.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis. PKs are also implicated in inflammatory conditions and in the multiplication of viruses and parasites. PKs can also play a major role in the pathogenesis and development of neurodegenerative disorders. PKs malfunctioning and disregulation are further discussed in Current Opinion in Chemical Biology 1999, 3, 459-465.

Among the several protein kinases known in the art as being implicated in the growth of cancer cells is Cdc7, an evolutionary conserved serine-threonine kinase which plays a pivotal role in linking cell cycle regulation to genome duplication, being essential for the firing of DNA replication origins (see Montagnoli A. et al., EMBO Journal, Vol. 21, No. 12, pp. 3171-3181, 2002; Montagnoli A. et al., Cancer Research Vol. 64, October 1, pp. 7110-7116, 2004).

Several heterocyclic compounds are known in the art as protein kinase inhibitors. Among them are, for instance, pyrrolo-pyrazoles disclosed in WO 02/12242; tetrahydroindazoles disclosed in WO 00/69846; pyrrolo-pyridines disclosed in WO 01/98299; aminophthalazinones disclosed in WO 03/014090 and aminoindazoles disclosed in WO 03/028720.

In addition, pyrrolopyridinone derivatives for the treatment of obesity are disclosed in the patent WO 2003/27114 to Bayer Pharmaceuticals Corporation. In particular a pyridylpyrrolopyridinone, namely 5-cyclohexyl-1-(2,4-dichloro-phenyl)-3-methyl-2-pyridin-3-yl-1,5,6,7-tetrahydro-pyrrolo[3,2-c]pyridin-4-one is reported.

Pyrrolopyridinone derivatives, endowed with mitogen activated protein kinase-activated protein kinase-2 inhibitory activity, are disclosed in the patent WO 2004/058762 A1 (priority December 2002, foreign filings December 2003) to Pharmacia Corp.

SUMMARY OF THE INVENTION

The invention relates to novel compounds which are useful, in therapy, as agents against a host of diseases caused by and/or associated to a disregulated protein kinase activity and, more particularly, Cdk2 and Cdc7 activity.

The invention also relates to compounds which have protein kinase inhibiting activity and, more particularly, Cdk2 and Cdc7 inhibiting activity.

One aspect of the invention relates to heteroarylpyrrolopyridinone derivatives which are represented by formula (I)

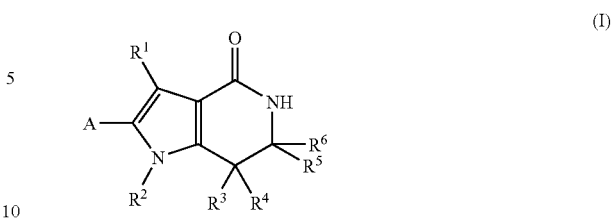

wherein

A is selected from the group consisting of pyridin-4-yl, 3-fluoro-pyridin-4-yl, and 2-amino-pyrimidin-4-yl;

$R^1$ is selected from the group consisting of hydrogen, halogen and $(C_1-C_6)$alkyl;

$R^2$ is selected from the group consisting of hydrogen, $(C_1-C_6)$alkyl, $(C_1-C_6)$alkenyl, $(C_1-C_6)$alkynyl, $(C_3-C_6)$cycloalkyl, $(C_1-C_6)$haloalkyl, $(C_1-C_6)$polyfluorinated alkyl, heterocyclyl, aryl, heteroaryl, $(C_3-C_6)$cycloalkyl-$(C_1-C_6)$alkyl, heterocyclyl-$(C_1-C_6)$alkyl, aryl-$(C_1-C_6)$alkyl, heteroaryl-$(C_1-C_6)$alkyl, $(C_1-C_8)$hydroxyalkyl, $(C_1-C_8)$alkoxy-$(C_1-C_8)$alkyl, aryloxy-$(C_1-C_8)$alkyl, heteroaryloxy-$(C_1-C_8)$alkyl, $(C_1-C_8)$aminoalkyl, $(C_1-C_8)$alkylamino-$(C_1-C_8)$alkyl, $(C_1-C_8)$dialkylamino-$(C_1-C_8)$alkyl, carbamoyl-$(C_1-C_8)$alkyl, and alkoxycarbonyl, wherein each of said aryl, heteroaryl, heterocyclyl, aryloxy, and heteroaryloxy moieties can be unsubstituted or substituted by one or more substituents, each substituent being independently selected from the group consisting of alkyl, aryl, $—OCF_3$, $—OC(O)$alkyl, $—OC(O)$aryl, $—CF_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

$R^3$, $R^4$, $R^5$ and $R^6$ are each independently selected from the group consisting of hydrogen, $(C_1-C_6)$haloalkyl, $(C_1-C_6)$polyfluorinated alkyl, $(C_1-C_6)$haloalkenyl, $(C_1-C_6)$polyfluorinated alkenyl, $(C_1-C_8)$hydroxyalkyl, $(C_1-C_8)$alkoxy-$(C_1-C_8)$alkyl, aryloxy-$(C_1-C_8)$alkyl, heteroaryloxy-$(C_1-C_8)$alkyl, aryl-$(C_1-C_8)$alkoxy-$(C_1-C_8)$alkyl, $(C_1-C_8)$azidoalkyl group, $(C_1-C_8)$aminoalkyl, $(C_1-C_8)$alkylamino-$(C_1-C_8)$alkyl, $(C_1-C_8)$dialkylamino-$(C_1-C_8)$alkyl, and $(C_1-C_8)$alkyl-OC(O)-amino$(C_1-C_8)$alkyl, with the proviso that at least one of: $R^3$, $R^4$, $R^5$ or $R^6$ is different from hydrogen;

or a pharmaceutically acceptable salt or solvate thereof.

Another aspect of the invention relates to a method of treating cell proliferative disorders or conditions, that can be caused by and/or associated with an altered protein kinase activity, by administering to a mammal in need of said treatment an amount of a compound of Formula (I).

Another aspect of the invention relates to a method of antagonizing activity toward Cdk2 or Cdc7, comprising administering to said Cdk2 or Cdc7 an amount of a compound of Formula (I) that is effective in antagonizing activity toward Cdk2 or Cdc7.

Another aspect of the invention relates to a method of treating a disorder or condition in a mammal, wherein antagonist activity toward Cdk2 or Cdc7 is needed in said mammal, comprising administering to said mammal an amount of a compound of Formula (I) that is effective in antagonizing activity toward Cdk2 or Cdc7.

Another aspect of the invention relates to a method of treating a disorder or condition in a mammal for which antagonist activity toward toward Cdk2 or Cdc7 is needed in said mammal, comprising administering to said mammal an amount of a compound of Formula (I) that is effective in treating said disorder or condition.

Another aspect of the invention relates to a method of treating a disorder or condition selected from the group consisting of bladder cancer, breast cancer, colon cancer, kidney cancer, liver cancer, lung cancer, including small cell lung cancer, esophagus cancer, gall-bladder cancer, ovarian cancer, pancreatic cancer, stomach cancer, cervical cancer, thyroid cancer, prostate cancer, and skin cancer, including squamous cell carcinoma, hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma, Burkitt's lymphoma, hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma, in a mammal, comprising administering to said mammal in need of said treatment an amount of a compound of Formula (I) that is effective in treating said condition or disorder.

Another aspect of the invention relates to a method of treating a disorder or condition selected from the group consisting of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis, in a mammal, comprising administering to said mammal in need of said treatment an amount of a compound of Formula (I) that is effective in treating said condition or disorder.

Another aspect of the invention relates to a method of treating a disorder or condition selected from the group consisting of bladder cancer, breast cancer, colon cancer, kidney cancer, liver cancer, lung cancer, including small cell lung cancer, esophagus cancer, gall-bladder cancer, ovarian cancer, pancreatic cancer, stomach cancer, cervical cancer, thyroid cancer, prostate cancer, and skin cancer, including squamous cell carcinoma, hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma, Burkitt's lymphoma, hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma, in a mammal, comprising administering to said mammal in need of said treatment an amount of a compound of Formula (I) that is effective in antagonizing activity toward Cdk2 or Cdc7.

Another aspect of the invention relates to a method of treating a disorder or condition selected from the group consisting of benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis, post-surgical stenosis and restenosis, in a mammal, comprising administering to said mammal in need of said treatment an amount of a compound of Formula (I) that is effective in antagonizing activity toward Cdk2 or Cdc7.

Another aspect of the invention relates to a pharmaceutical composition comprising an amount of the compound of Formula (I), or a pharmaceutically acceptable salt or solvate thereof, and a pharmaceutically acceptable carrier.

Preferably, specific types of cancer that can be treated from those listed above include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

A more complete appreciation of the invention, and many of the attendant advantages thereof, will be readily understood as the same becomes better understood by reference to the following detailed description.

DETAILED DESCRIPTION OF THE INVENTION

One aspect of the invention relates to heteroarylpyrrolopyridinone derivatives which are represented by formula (I)

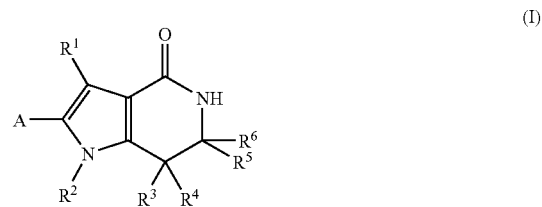

wherein

A is selected from the group consisting of pyridin-4-yl, 3-fluoro-pyridin-4-yl, and 2-amino-pyrimidin-4-yl;

$R^1$ is selected from the group consisting of hydrogen, halogen and $(C_1-C_6)$alkyl;

$R^2$ is selected from the group consisting of hydrogen, $(C_1-C_6)$alkyl, $(C_1-C6)$alkenyl, $(C_1-C_6)$alkynyl, $(C_3-C_6)$cycloalkyl, $(C_1-C_6)$haloalkyl, $(C_1-C_6)$polyfluorinated alkyl, heterocyclyl, aryl, heteroaryl, $(C_3-C_6)$cycloalkyl-$(C_1-C_6)$alkyl, heterocyclyl-$(C_1-C_6)$alkyl, aryl-$(C_1-C_6)$alkyl, heteroaryl-$(C_1-C_6)$alkyl, $(C_1-C_8)$hydroxyalkyl, $(C_1-C_8)$alkoxy-$(C_1-C_8)$alkyl, aryloxy-$(C_1-C_8)$alkyl, heteroaryloxy-$(C_1-C_8)$alkyl, $(C_1-C_8)$aminoalkyl, $(C_1-C_8)$alkylamino-$(C_1-C_8)$alkyl, $(C_1-C_8)$dialkylamino-$(C_1-C_8)$alkyl, carbamoyl-$(C_1-C_8)$alkyl, and alkoxycarbonyl, wherein each of said aryl, heteroaryl, heterocyclyl, aryloxy, and heteroaryloxy moieties can be unsubstituted or substituted by one or more substituents, each substituent being independently selected from the group consisting of alkyl, aryl, —OCF$_3$, —OC(O)alkyl, —OC(O)aryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

$R^3$, $R^4$, $R^5$ and $R^6$ are each independently selected from the group consisting of hydrogen, ($C_1$-$C_6$)haloalkyl, ($C_1$-$C_6$) polyfluorinated alkyl, ($C_1$-$C_6$)haloalkenyl, ($C_1$-$C_6$)polyfluorinated alkenyl, ($C_1$-$C_8$)hydroxyalkyl, ($C_1$-$C_8$)alkoxy-($C_1$-$C_8$)alkyl, aryloxy-($C_1$-$C_8$)alkyl, heteroaryloxy-($C_1$-$C_8$) alkyl, aryl-($C_1$-$C_8$)alkoxy-($C_1$-$C_8$)alkyl, ($C_1$-$C_8$)azidoalkyl group, ($C_1$-$C_8$)aminoalkyl, ($C_1$-$C_8$)alkylamino-($C_1$-$C_8$)alkyl, ($C_1$-$C_8$)dialkylamino-($C_1$-$C_8$)alkyl, and ($C_1$-$C_8$)alkyl-OC (O)-amino($C_1$-$C_8$)alkyl, with the proviso that at least one of: $R^3$, $R^4$, $R^5$ or $R^6$ is different from hydrogen;

or a pharmaceutically acceptable salt or solvate thereof.

The compounds of formula (I) of the invention can have asymmetric carbon atoms and can therefore exist as individual optical isomers, as racemic admixtures or as any other admixture including a majority of one of the two optical isomers, which are all to be intended as comprised within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention. Prodrugs are any covalently bonded compounds which release the active parent drug, according to formula (I), in vivo.

In cases when compounds can exist in tautomeric forms, for instance keto-enol tautomers, each tautomeric form is contemplated as being included within this invention whether existing in equilibrium or predominantly in one form.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkylamino", "dialkylamino", aryl-($C_1$-$C_8$)alkoxy-($C_1$-$C_8$) alkyl, etc.

"Mammal" means humans and other animals.

"Treating" refers to, and includes, reversing, alleviating, inhibiting the progress of, or preventing, a disease, disorder or condition, or one or more symptoms thereof; and, "treatment" and "therapeutically" refer to the act of treating, as defined above.

The term "effective amount" means an amount of compound of the present invention that is capable of treating a specific disease or antagonizing a specific enzyme, such as a specific protein kinase. The particular dose of compound administered according to the invention will be determined by the particular circumstances surrounding the case including, for example, the compound administered, the route of administration, the state of being of the subject, and the severity of the pathological condition being treated.

"Alkyl" means an aliphatic hydrocarbon group, which can be straight or branched. Branched means that one or more alkyl groups, such as methyl, ethyl or propyl, are attached to a linear alkyl chain. Nonlimiting examples of alkyl groups include methyl, ethyl, n-propyl, isopropyl, n-butyl, isobutyl, tert-butyl, sec-butyl, n-pentyl, n-hexyl, and the like. The alkyl group can be unsubstituted or substituted by one or more substituents which can each be independently selected from the group consisting of halo, alkyl, aryl, aralkyl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl, isobutyl, sec-butyl, n-pentyl, n-hexyl, and the like.

"Alkenyl" means an aliphatic hydrocarbon group containing at least one carbon-carbon double bond and which can be straight or branched. The alkenyl group can be unsubstituted or substituted by one or more substituents which can be the same or different, each substituent being independently selected from the group consisting of halo, alkyl, aryl, cycloalkyl, cyano, and alkoxy. Non-limiting examples of suitable alkenyl groups include ethenyl, propenyl, and n-butenyl.

"Alkynyl" means an aliphatic hydrocarbon group containing at least one carbon-carbon triple bond and which can be straight or branched. Branched means that one or more lower alkyl groups such as methyl, ethyl or propyl, are attached to a linear alkynyl chain. Non-limiting examples of suitable alkynyl groups include ethynyl, propynyl, and 2-butynyl. The alkynyl group can be unsubstituted or substituted by one or more substituents each being independently selected from the group consisting of alkyl, aryl and cycloalkyl.

"amino" means an —NH$_2$ group whilst the term arylamino comprises any group —NH-aryl, wherein aryl is as defined below.

"halogen" or "halo" means a fluorine, chlorine, bromine or iodine atom.

"polyfluorinated alkyl" means any alkyl group as defined above being substituted by two or more fluorine atoms such as, for instance, trifluoromethyl, 2,2,2-trifluoroethyl, 3,3,3-trifluoropropyl, 1,1-difluoroethyl, 3,3-difluoropropyl and the like.

"aryl" means any carbocyclic or heterocyclic hydrocarbon with from 1 to 2 ring moieties, either fused or linked to each other by single bonds, wherein at least one of the rings is aromatic. If present, any aromatic heterocyclic hydrocarbon also referred to as "heteroaryl" group, comprises a 5 to 6 membered ring with from 1 to 3 heteroatoms selected among N, O or S.

The aryl or heteroaryl group can be unsubstituted or substituted on the ring with one or more substituents, each being independently selected from the group consisting of alkyl, aryl, —OCF$_3$, —OC(O)alkyl, —OC(O)aryl, —CF$_3$, heteroaryl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodibxolyl, indanyl, indenyl, triazolyl, and the like.

"cycloalkyl" means a non-aromatic mono- or multicyclic ring system. The cycloalkyl can be unsubstituted or substituted on the ring by replacing an available hydrogen on the ring by one or more substituents, each being independently selected from the group consisting of alkyl, aryl, heteroaryl, aralkyl, alkylaryl, aralkenyl, heteroaralkyl, alkyiheteroaryl, heteroaralkenyl, hydroxy, hydroxyalkyl, alkoxy, aryloxy, aralkoxy, acyl, aryl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —NH(alkyl), —NH(cycloalkyl), and —N(alkyl)$_2$. Non-limiting examples of suitable monocyclic cycloalkyls include cyclopropyl, cyclobutyl, cyclopentyl and cyclohexyl.

"heterocyclyl" or "heterocycle" means any 5 or 6 membered heterocyclic ring comprising from 1 to 3 heteroatoms selected among N, O or S. If the said heterocycle or heterocyclyl group is an aromatic heterocycle, also referred to as heteroaryl, it is encompassed by the above definition given to aryl groups.

As such, besides the above aromatic heterocycles, the term heterocyclyl also encompasses saturated or partially unsaturated heterocycles such as, for instance, pyrroline, pyrrolidine, imidazoline, imidazolidine, pyrazoline, pyrazolidine, piperidine, piperazine, morpholine, and the like. The heterocyclyl group can be unsubstituted or substituted on the ring with one or more substituents, each being independently selected from the group consisting of alkyl, aryl, —OCF$_3$, —OC(O)alkyl, —OC(O)aryl, —CF$_3$, heteroaryl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$.

In this respect, as an example, any group which is identified as an arylalkyl has to be intended as an alkyl group which is further substituted by aryl, wherein both aryl and alkyl are as above defined. Clearly when $R^3$ and $R^4$ or $R^5$ and $R^6$, taken together, form a ($C_3$-$C_6$)cycloalkyl group, the compound is referred to as spiro derivative.

"Alkoxy" refers to a radical of the formula —O-alkyl, wherein alkyl is as defined above. Non-limiting examples of alkoxy includes methoxy, ethoxy, n-propoxy, 1-methylethoxy (iso-propoxy), n-butoxy, n-pentoxy, 1,1-dimethylethoxy (t-butoxy), and the like.

"Aryloxy" refers to a radical of the formula —O-aryl, wherein aryl is as defined above.

"Heteroaryloxy" refers a radical of the formula —O-heteroaryl, wherein heteroaryl is as defined above.

Pharmaceutically acceptable salts of the compounds of formula (I) include the acid addition salts with inorganic or organic acids such as, for instance, nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of formula (I) or a salt and/or solvate thereof. A discussion of prodrugs is provided in T. Higuchi and V. Stella, Pro-drugs as Novel Delivery Systems (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

A preferred class of compounds of the invention is represented by the derivatives of formula (I) wherein A is as defined above, $R^1$, $R^2$, $R^5$ and $R^6$ are as defined above and both $R^3$ and $R^4$ are hydrogen atoms.

Another preferred class of compounds of the invention is represented by the derivatives of formula (I) wherein A is as defined above, $R^1$, $R^2$, $R^3$ and $R^4$ are as defined above and both $R^5$ and $R^6$ are hydrogen atoms.

More preferred compounds of the invention, within the above classes, are the derivatives of formula (I) wherein A is as defined above, $R^1$ is a hydrogen atom, $R^2$, $R^3$ are as defined above and $R^4$, $R^5$, $R^6$ are hydrogen atoms.

More preferred compounds of the invention, within the above classes, are the derivatives of formula (I) wherein A is as defined above, $R^1$ is a hydrogen atom, $R^2$, $R^5$ are as defined above and $R^3$, $R^4$ and $R^6$ are hydrogen atoms.

The compounds of formula (I) can be obtained by the following schemes, which are described in detail hereinbelow:

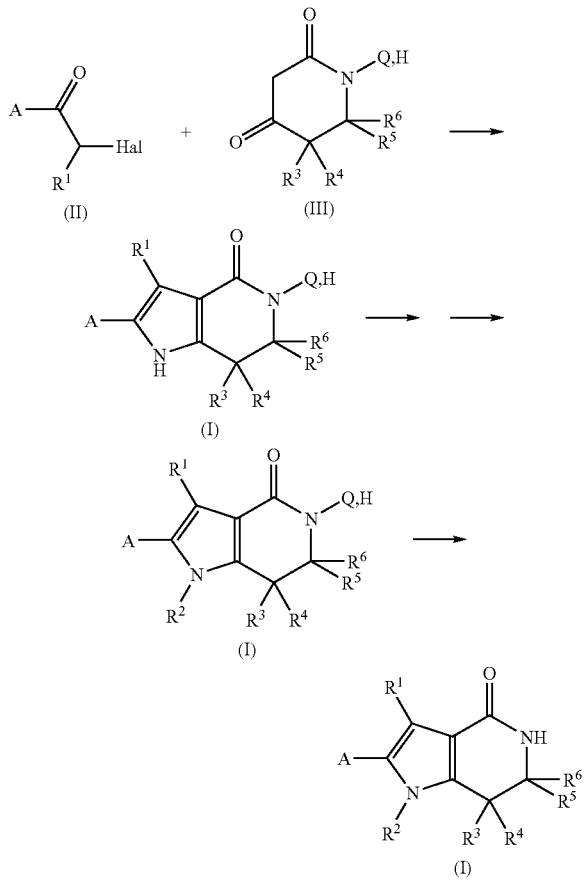

SCHEME 1

SCHEME 2
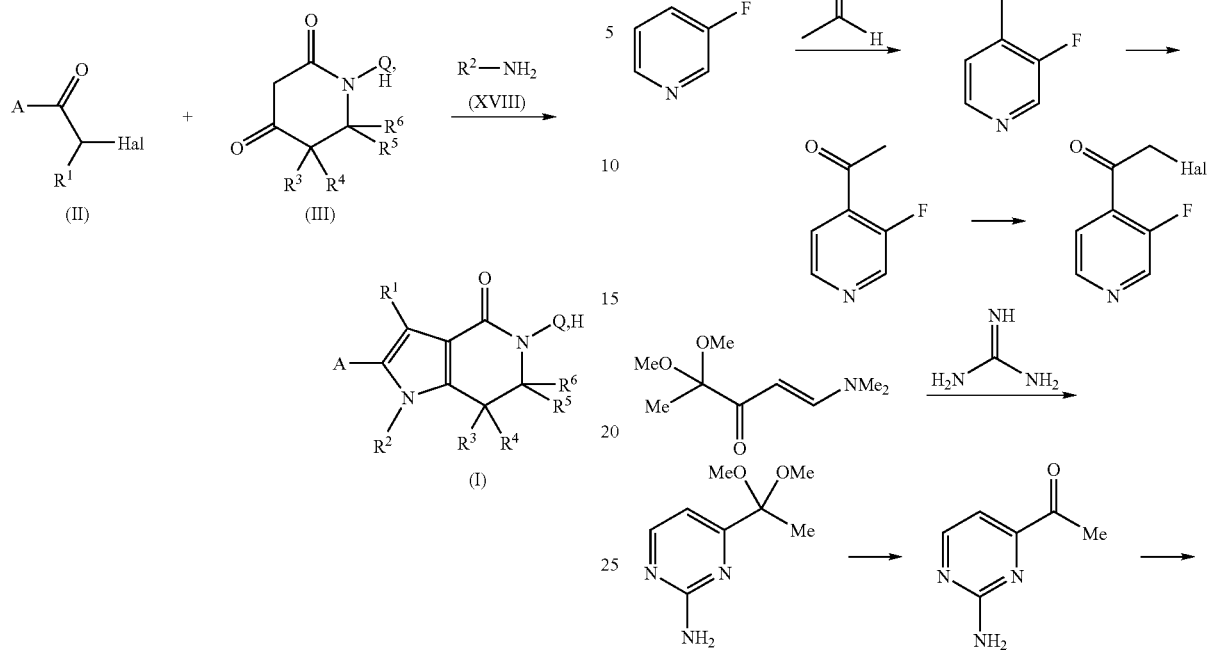
SCHEME 3
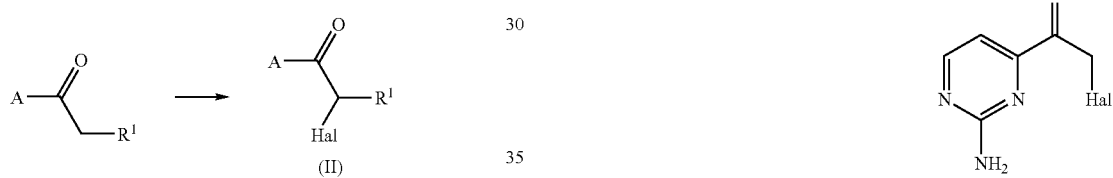
SCHEME 4
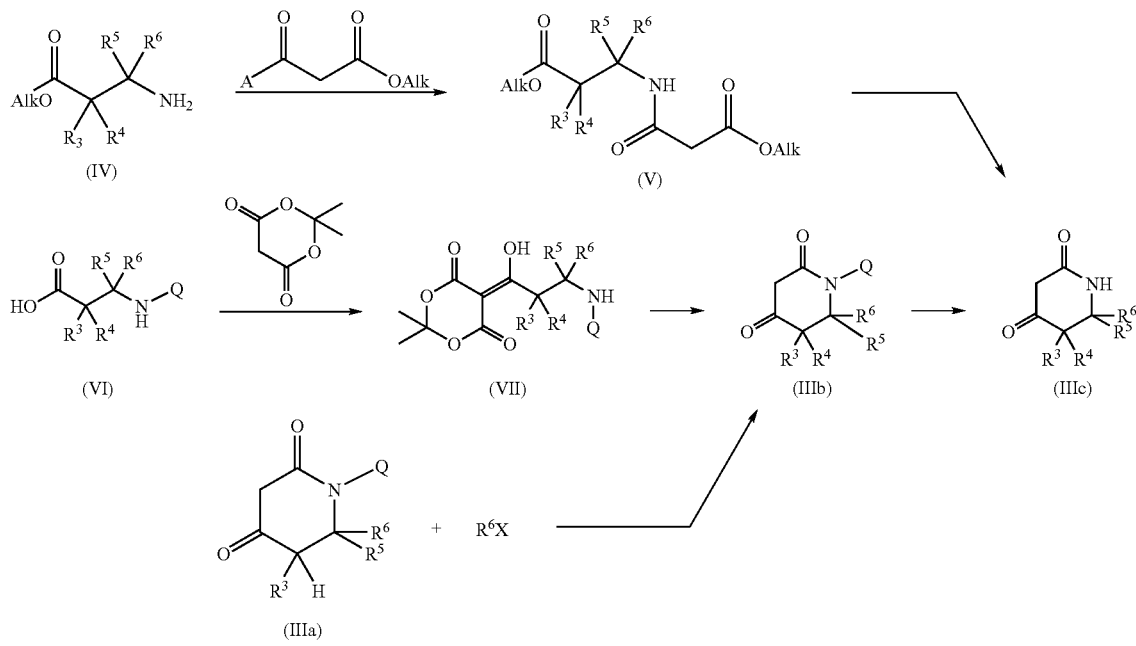

SCHEME 5

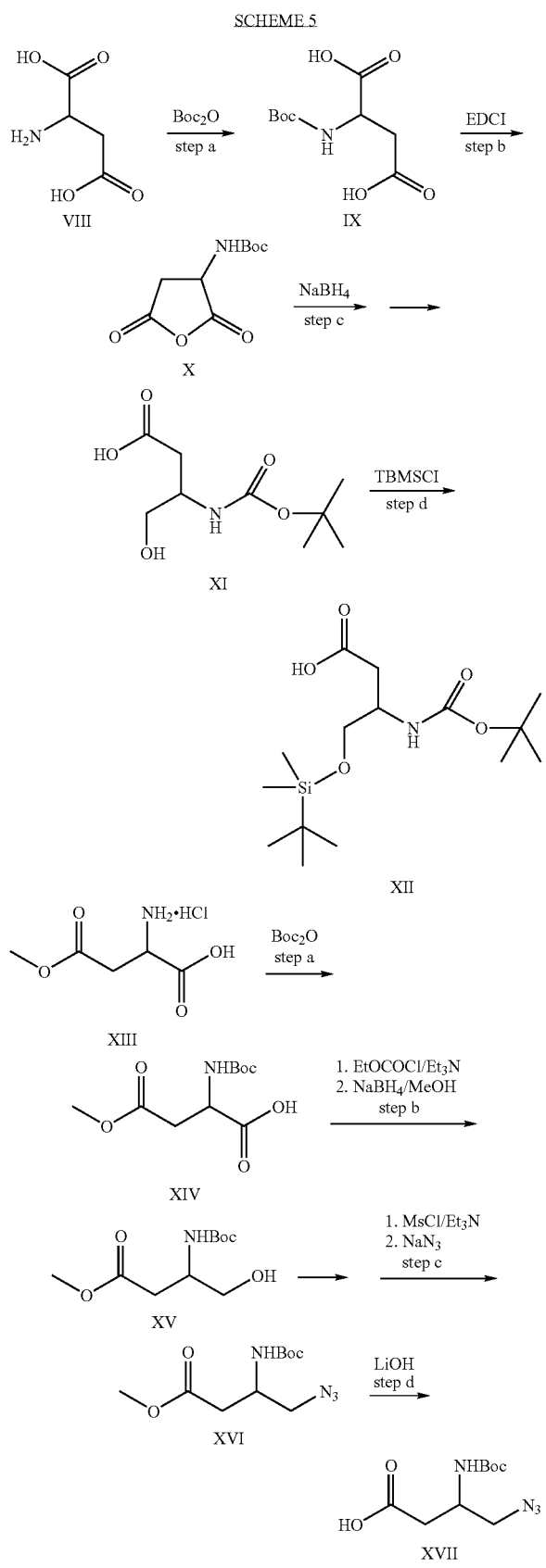

The compounds of formula (I, $R^2$=H) can be prepared according to the following synthetic scheme, by reacting the heteroaryl derivative of formula (II) with a suitable piperidine-2,4-dione derivative of formula (III) wherein Q is H or a suitable nitrogen protecting group, preferably tert-butoxycarbonyl or, for example, a group like p-methoxybenzyl, p-methoxyethylbenzyl, p-methoxyphenyl group.

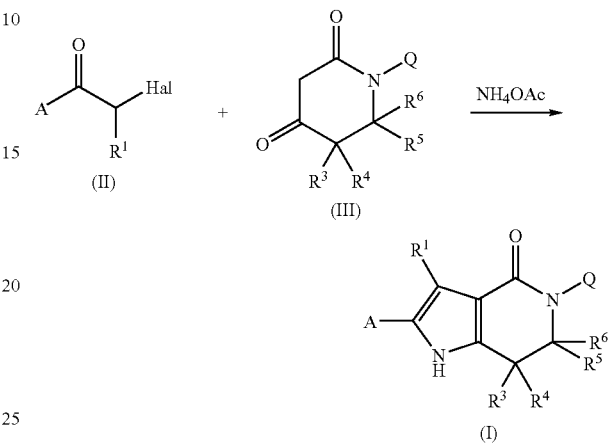

The reaction occurs in the presence of ammonium acetate in a suitable solvent such as, for instance, a lower alcohol or acetic acid. Preferably, the reaction is carried out in the presence of ethanol by working at room temperature and for a suitable period of time varying from about 2 hours to about 24 hours.

The compounds of formula (II) and (III), as well as any other reactant of the process, are known or, if not commercially available per se, they can be easily prepared according to known methods.

As an example, the heteroaryl derivatives of formula (II) can be prepared by halogenating, e.g. brominating or chlorinating, a suitable heteroaryl-ethanone derivative, according to the following pathway:

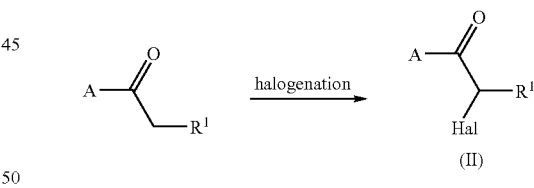

The reaction occurs by working under conventional methods, for instance in the presence of bromine and in a suitable solvent such as a mixture of acetic and hydrobromic acid, for a time varying between about 1 hour and about 24 hours. Alternatively, a suitably activated heteroaryl derivative, e.g. an enolether or silylether, can be reacted with a halogen source, for instance N-bromo-succinimide (NBS), in a suitable solvent, such as tetrahydrofuran/water mixtures.

Non-limiting examples of suitable heteroaryl-ethanone derivatives which can be halogenated include 1-pyridin-4-ylethanone, 1-pyridin-4-ylpropan-1-one, 1-(3-fluoropyridin-4-yl)ethanone and 1-(2-aminopyrimidin-4-yl)ethanone.

1-(3-Fluoropyridin-4-yl)ethanone can be prepared, for example, by reacting commercial 3-fluoropyridine with acetaldehyde in the presence of a base, such as, for example, lithiumdiisopropylamide (LDA) and oxidizing the so obtained 1-(3-fluoropyridin-4-yl)ethanol by means of, for instance, manganese dioxide in a suitable solvent, like toluene. 1-(2-Aminopyrimidin-4-yl)ethanone can be obtained according to the following path:

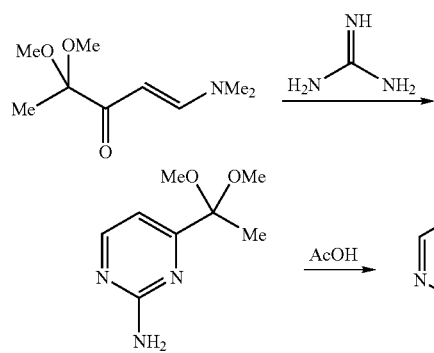

1-(Dimethylamino)-4,4-dimethoxy-1-penten-3-one is a known compound which can be prepared according to known methods, for instance as reported in *J. Het. Chem.*, 22(6), 1723-6, 1985. It is easily reacted with guanidine, for instance being available in the form of an acid addition salt, e.g. as guanidinium hydrochloride salt. The reaction is carried out under basic conditions, for instance in the presence of sodium ethylate and of a suitable solvent such as a lower alcohol, preferably ethanol. The reaction occurs at refluxing temperature, for a suitable time up to about 24 hours.

The above reaction leads to the aminopyrimidine nucleus which is then converted into the final intermediate through acidic treatment at room temperature, for instance in the presence of acetic acid.

Also the piperidine-2,4-dione derivative (III) is a known compound or, alternatively, can be prepared by known methods, for instance according to the synthetic pathway below, wherein Alk stands for a suitable lower alkyl group, e.g. ethyl, and A stands for chloro or OAlk:

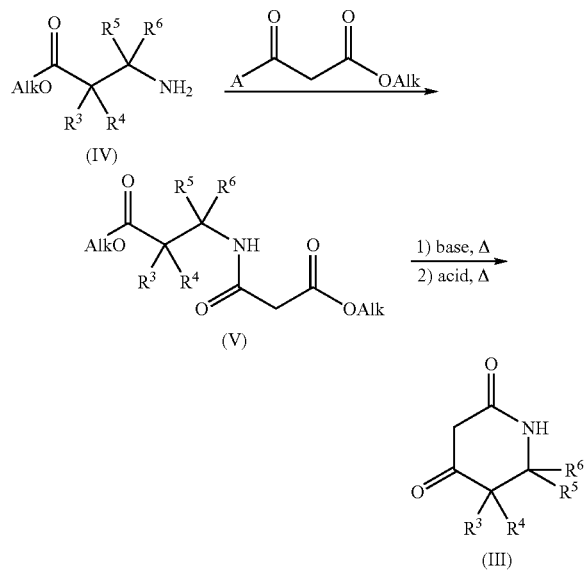

In this respect, a suitable β-amino-carboxyester (IV) derivative wherein $R^3$, $R^4$, $R^5$ and $R^6$ have the above reported meanings, is reacted with dialkylmalonate or, alternatively, with 3-chloro-3-oxopropanoic acid alkyl ester, for instance, dimethylmalonate or ethyl 3-chloro-3-oxopropanoate, respectively. When A is chloro the reaction is carried out under basic conditions, for instance in the presence of triethylamine, and in a suitable solvent such as dichloromethane, at a temperature comprised between room temperature to reflux. When A is Oalk, the reaction is carried out with or without basic conditions and more conveniently, in the absence of solvents, at reflux temperature of the dialkylmalonate.

When not commercially available, the above-mentioned β-amino-carboxyester derivatives (IV) can be obtained according to well-known procedures described in the literature.

The intermediate derivative thus obtained (V) is then converted into the compound of formula (III), first by reacting it under basic conditions, e.g. in the presence of sodium methylate and of a suitable solvent, preferably toluene, at refluxing temperature and for a time varying between about 2 hours and about 24 hours. Subsequently, the product of the former step is reacted as such, without being isolated, with an acetonitrile/water/acetic acid mixture under refluxing conditions and for a time varying between about 12 hours and about 24 hours.

In the alternative, the piperidine-dione derivative (III) can be prepared, for instance, according also to the synthetic pathway below:

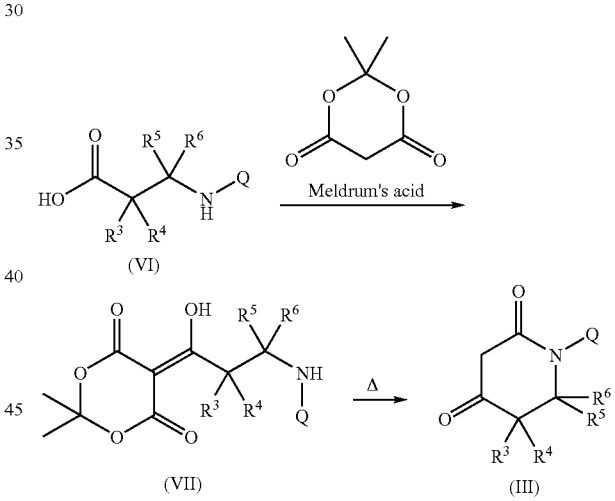

In the procedure, Meldrum's acid is reacted with a suitable aminoacid derivative of formula (VI) so as to obtain a compound of formula (VII) wherein Q is a suitable nitrogen protecting group and $R^3$, $R^4$, $R^5$ and $R^6$ are as above defined. The compound of formula (VII) is then cyclized by dissolving it in a suitable solvent, for instance ethylacetate, and refluxing for a period of time from 1 to 24 hours.

The aminoacid derivative (VI) is a known compound or, alternatively, can be prepared by known methods, according to well known procedures described in the literature.

For instance, DL-3-tert-butoxycarbonylamino-4-(tert-butyl-dimethyl-silanyloxy)-butyric acid (XII) can be synthesized following the synthetic scheme depicted below. In the procedure, DL aspartic acid (VIII) is reacted with di-tert-butyl dicarbonate ($Boc_2O$) so as to obtain product (IX); in the presence of 1-(3-dimethylaminopropyl)-3-ethylcarbodiimide hydrochloride (EDCI) compound (IX) is converted into (2,4-dioxo-cyclopentyl)-carbamic acid tert-butyl ester (X), that is reduced with sodium borohydride to afford product (XI).

By subsequent protection with tert-butyldimethylsilyl chloride, the desired compound (XII) is then obtained.

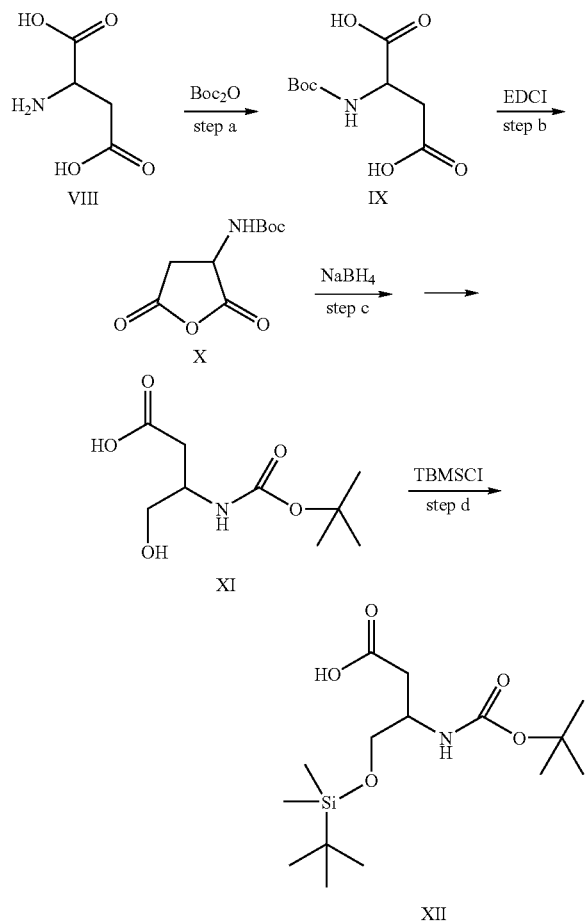

According to step (a) of the process, DL aspartic acid (VIII) is reacted with di-tert-butyl dicarbonate in the presence of N,N-diisopropylethylamine. The reaction can be carried out in a mixture of solvents such as, for instance, dioxane and water at a temperature ranging from about 0° C. to about 10° C.

As in step (b) of the process, the compound of formula (IX) is reacted with 1-(3-dimethylaminopropyl)-3-ethylcarbodiimide hydrochloride in a variety of solvents including chloroform, dichloromethane, dimethylformamide. Stirring is maintained at a temperature ranging from about 0° C. to room temperature for a suitable time varying from about 4 hours to about 10 hours.

According to step (c), the compound of formula (X) is converted into the hydroxy derivative (XI) through reaction with a suitable reducing agent, such as, for instance, sodium borohydride. The reaction can be carried out in tetrahydrofuran. In this respect, the solution of sodium borohydride is cooled to 0° C., and the compound (X) is added dropwise. Stirring is maintained for a suitable time from about 1 hour to 3 hours.

According to step (d), tert-butyldimethylsilyl chloride (TBDMSCl) is reacted with the compound (XI) in the presence of imidazole. The reaction can be carried out in a suitable solvent such as, for instance, dichloromethane, dimethylformamide, while stirring is maintained for a time varying from about 5 hours to 10 hours.

Another example of preparation of an aminoacid derivative (VI) is represented by DL-4-azido-3-tert-butoxycarbony-lamino-butyric acid (XVII) that can be synthesized as depicted in the scheme below:

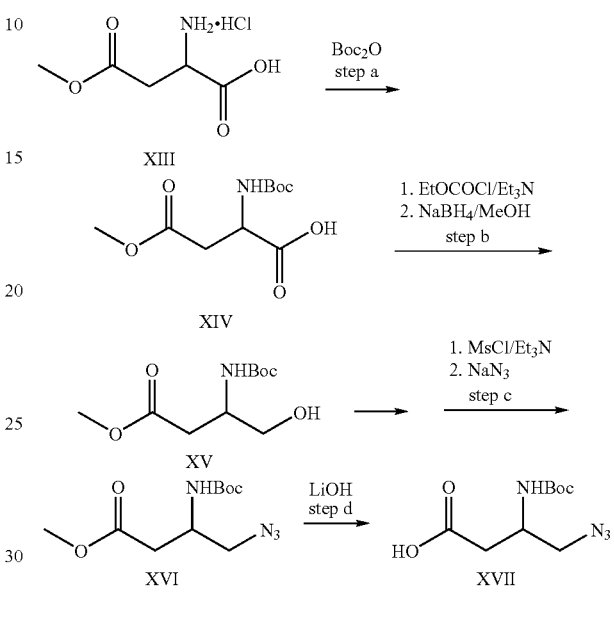

In the procedure, DL-2-amino-succinic acid 4-methyl ester (XIII) is reacted with di-tert-butyl dicarbonate (Boc$_2$O) so to obtain product (XIV) that is reduced with sodium borohydride so to afford product (XV). Hydroxyl activation as mesilate and its nucleophilic substitution by the azido group provide the desired compound (XVI) that is finally hydrolyzed in basic conditions to acid (XVII).

According to step (a) of the process DL-2-amino-succinic acid 4-methyl ester (XIII) is reacted with di-tert-butyl dicarbonate in the presence of a base, for instance sodium carbonate. The reaction can be carried out in a mixture of solvents such as, for instance, dioxane and water at a temperature ranging from about 0° C. to room temperature.

As in step (b) of the process, the compound of formula (XIV) is reacted with ethyl chloroformate in the presence of triethylamine and rapidly treated with sodium borohydride at 0° C. for about one hour, then stirring is maintained at room temperature for a suitable time varying from about 1 hour to about 4 hours.

According to step (c) (first part), the alcohol of formula (XV) is converted into the corresponding mesylate derivative through reaction with methanesulfonyl chloride in a suitable solvent, for example, dichloromethane at 0° C. for a convenient period of time, from about 30 'to about 1 hour, and then stirring at room temperature is maintained for a suitable time from about 1 hour to about 3 hours. Step (c) (second part) deals with the transformation of mesylate into the azido group (compound XVI) by means of sodium azide in dimethylformamide at temperature between about 40 and about 80° C. for a period of time from about 1 hour to about 8 hours.

According to step (d), hydrolysis of the methyl ester is carried out in basic conditions, for instance, in the presence of lithium hydroxide. The reaction can be carried out in a suitable mixture of solvents such as, for instance, tetrahydrofuran/water, while stirring is maintained for a period of time ranging from about 1 hour to about 4 hours.

In the alternative, a piperidine-dione (ill) can be transformed in another piperidine-dione (III), for example according to the synthetic pathway below, wherein Q stands for a suitable nitrogen-protecting group such as, in particular, tert-butoxycarbonyl, or other groups, such as, for example, p-methoxyphenyl, and X is halide, triflate, mesylate, tosylate and the like.

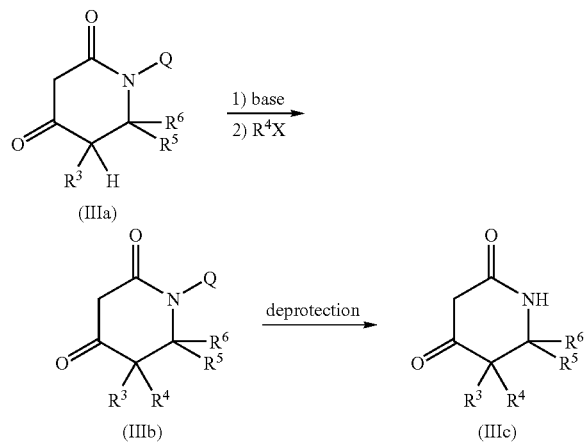

In this respect, a suitable piperidine-dione derivative (IIIa) wherein $R^3$, $R^5$ and $R^6$ and Q have the above reported meanings, is reacted with a base, for instance lithium bis(trimethylsilyl)amide (LiHMDS). The reaction is carried out in a suitable solvent such as tetrahydrofuran, at a temperature comprised between −78° C. and room temperature.

The reaction mixture is then treated with a suitable $R^4X$, where X is a group such as halide, triflate, mesylate, tosylate and the like, thus obtaining a compound of formula (IIIb). The compound thus obtained can be converted into the compound of formula (IIIc) by treating it, for instance, when Q is a tert-butoxycarbonyl group, with acidic conditions, e.g. in the presence of trifluoroacetic acid and of a suitable solvent, preferably dichloromethane, at room temperature and for a time comprised between about 1 hour and about 6 hours.

The final compound of formula (I) thus obtained can be then converted into another compound of formula (I) according to well-known methods in the art. As an example, the compounds of formula (I) wherein $R^1$ represents a hydrogen atom can be easily converted into the corresponding compounds wherein $R^1$ is a halogen atom, through conventional methods reported in the literature for the halogenation of pyrrole derivatives.

The compounds of formula (I), where $R^2$ is different from hydrogen atom, can be obtained by different general procedures, for instance, by N-derivatization of the pyrrole nitrogen atom of compounds of formula (I), where $R^2$ is hydrogen, by reacting them with electrophiles $R^2$—X, where X can be, for example, halide, triflate, mesylate, tosylate and the like, so that a compound with $R^2$ as defined is obtained.

In another embodiment, the compounds of formula (I), where $R^2$ is different from hydrogen atom, can be prepared by N-derivatization of the pyrrole nitrogen atom of compounds of formula (I), where $R^2$ is hydrogen, by reacting them with an alcohol via Mitsunobu reaction.

In another embodiment, the compounds of formula (I), where $R^2$ is different from hydrogen atom can be also prepared by direct construction from simpler constituents, for instance via a Hantzsch type reaction.

As discussed above, the compounds of formula (I), where $R^2$ is as defined; can be prepared by reacting the pyrrolopyridinones of formula (I), where $R^2$ is an hydrogen atom, with a suitable electrophile, such as a convenient halide or a triflate, in a suitable solvent, such as dimethylformamide, THF, dioxane, in the presence of a suitable base, such as sodium hydride, at temperatutes ranging from −30° C. to room temperature, preferably at about 0° C., for a period of time ranging from about 1 hour to about 24 hours.

Alternatively a different base can be used, for instance potassium or cesium carbonate, optionally in the presence of a crown ether, for example 18-crown-6, at temperatures from about room temperature to about 100° C., optionally in a microwave cavity, in a suitable solvent, such as DMF.

The compounds of formula (I), where $R^2$ is as defined above, can be prepared also by reacting the pyrrolopyridinones of formula (I), where $R^2$ is a hydrogen atom, with a suitable alcohol, via the Mitsunobu reaction, in a suitable solvent, such as dimethylformamide, THF, dichloromethane, in the presence of triphenylphosphine and dialkylazodicarboxylate, for instance diethylazodicarboxylate, at temperatures ranging from about −78° C. to about reflux, for a period of time ranging from about 1 hour to 24 hours.

The compounds of formula (I), where $R^2$ is as defined, can be prepared also by reacting the pyrrolopyridinones of formula (I), where $R^2$ is a hydrogen atom, with a suitable alcohol, via the Mitsunobu reaction, in a suitable solvent, such as dimethylformamide, THF, or dichloromethane. The Mitsunobu reaction can be carried out in the presence of triphenylphosphine and dialkylazodicarboxylate, for instance diethylazodicarboxylate, at temperatures ranging from −78° C. to reflux, for a period of time ranging from about 1 hour to 24 hours.

According to an alternative approach, the compounds of formula (I) can be also directly prepared according to the following synthetic scheme, by reacting the above described heteroaryl derivative of formula (II) with a suitable piperidine-dione derivative of formula (III) wherein Q is H or the aforementioned nitrogen protecting group, preferably tert-butoxycarbonyl group, in the presence of a suitable amine of formula (XVIII), where $R^2$ is as defined.

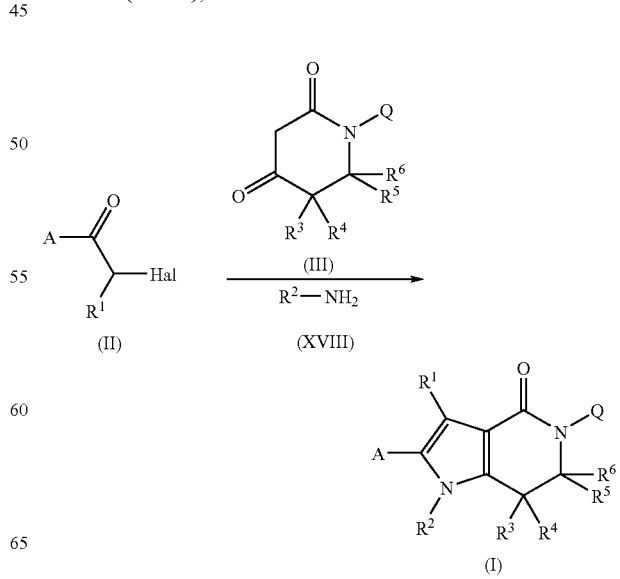

The reaction occurs in the presence of a suitable solvent such as, for instance, a lower alcohol or acetic acid. Preferably, the reaction is carried out in the presence of ethanol by working at temperatures ranging from about room temperature to about 100° C. and for a suitable time varying from about 2 hours to about 24 hours.

When Q is a protecting group, for instance a tert-butoxycarbonyl group, the desired compound of formula (I), where Q=H, can be obtained by treating it with acidic conditions, e.g. in the presence of trifluoroacetic acid and of a suitable solvent, preferably dichloromethane, at room temperature and for a time ranging from about 1 hour and about 6 hours.

Likewise, the conversion of a compound of formula (I) into a pharmaceutically acceptable salt is easily carried out according to known methods, e.g. by contacting any free base of formula (I) with any suitable pharmaceutically acceptable acid.

From all of the above, it is clear to the skilled person that when preparing the compounds of formula (I) according to the aforementioned processes, comprehensive of any variant thereof, optional functional groups within the starting materials or the intermediates thereof and which could give rise to unwanted side reactions, need to be properly protected according to conventional techniques. Likewise, the conversion of these latter into the free deprotected compounds can be carried out according to known procedures.

By analogy, any compound of formula (I) which is susceptible of being salified can be easily converted into the corresponding acid addition salt, by working in the presence of any pharmaceutically acceptable acid, for instance selected among those previously reported.

As it will be readily appreciated, if the compounds of formula (I) prepared according to the process described above are obtained as a mixture of isomers, their separation into the single isomers of formula (I), according to conventional techniques, is also within the scope of the present invention.

Conventional techniques for racemate resolution include, for instance, partitioned crystallization of diastereoisomeric salt derivatives or preparative chiral HPLC.

Pharmacology

The compounds of formula (i) are active as protein kinase inhibitors and are therefore useful, for instance, to restrict the unregulated proliferation of tumor cells. In therapy, they can be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

The inhibition assay of Cdc7/Dbf4 activity is performed according to the following protocol.

The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}$P phosphorylated MCM2 substrate remains in solution. The supernatant is collected, transferred into Optiplate plates and the extent of substrate phosphorylation is evaluated by β counting.

The inhibition assay of Cdc7/Dbf4 activity was performed in 96 wells plate according to the following protocol.

To each well of the plate were added:
- 10 μl test compound (10 increasing concentrations in the nM to uM range to generate a dose-response curve). The solvent for test compounds contained 3% DMSO. (final concentration 1%)
- 10 μl substrate MCM2 (6 mM final concentration), a mixture of cold ATP (2 mM final concentration) and radioactive ATP (1/5000 molar ratio with cold ATP).
- 10 μl enzyme (Cdc7/Dbf4, 2 nM final concentration) that started the reaction. The buffer of the reaction consisted in 50 mM HEPES pH 7.9 containing 15 mM $MgCl_2$, 2 mM DTT, 3 uM $NaVO_3$, 2 mM glycerophosphate and 0.2 mg/ml BSA.
- After incubation for 60 minutes at room temperature, the reaction was stopped by adding to each well 150 μl of Dowex resin in the presence of 150 mM formic acid. After another 60 min incubation, 50 μL of suspension were withdrawn and transferred into 96-well OPTIPLATEs containing 150 μl of MicroScint 40 (Packard); after 5-10 minutes shaking the plates were read for 1 min in a Packard TOP-Count radioactivity reader.

$IC_{50}$ determination: inhibitors were tested at different concentrations ranging from 0.0005 to 10 μM. Experimental data were analyzed by the computer program Assay Explorer using the four parameter logistic equation:

$$y = \text{bottom} + (\text{top} - \text{bottom})/(1 + 10^{((\log IC_{50} - x)*\text{slope})})$$

where x is the logarithm of the inhibitor concentration, y is the response; y starts at bottom and goes to top with a sigmoid shape.

In addition the selected compounds have been characterized for specificity on Cdk2A, on a panel of ser/threo kinases strictly related to cell cycle (Cdk2/cyclin E, Cdk1/cyclin B1, Cdk4/Cyclin D1, Cdk5/p25), on IGF1-R, Aurora-2, AKT1.

Inhibition Assay of Cdk2/Cyclin A Activity

Kinase reaction: 1.5 μM histone H1 substrate, 25 μM ATP (0.2 μCi P33 γ-ATP), 30 ng of baculovirus co-expressed Cdk2/Cyclin A, 10 μM inhibitor in a final volume of 100 μl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 μl EDTA 120 mM.

Capture: 100 μl were transferred from each well to MultiScreen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency ($IC_{50}$) as well as the kinetic-profile of inhibitor through Ki calculation.

$IC_{50}$ determination: the protocol used was the same described above, where inhibitors were tested at different concentrations ranging from 0.0045 to 10 μM. Experimental data were analyzed by the computer program GraphPad Prizm using the four parameter logistic equation:

$$y = \text{bottom} + (\text{top} - \text{bottom}) / (1 + 10^{((\log IC_{50} - x)*\text{slope})})$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 μM for ATP (containing proportionally diluted $p^{33}$ γ-ATP) and 0.4, 0.8, 1.2, 2.4, 4.8 μM for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

Inhibition Assay of Cdk2/Cyclin E Activity

Kinase reaction: 1.5 μM histone H1 (Sigma # H-5505) substrate, 25 μM ATP (0.2 μCi $p^{33}$ γ-ATP), 15 ng of baculovirus co-expressed cdk2/GST-Cyclin E, suitable concentrations of inhibitor in a final volume of 100 μl buffer (TRIS HCl 10 mM pH 7.5, $MgCl_2$ 10 mM, 7.5 mM DTT+0.2 mg/ml BSA) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl /well scintillant were added and $^{33}P$ labeled histone H1 was detected by radioactivity counting in the Top-Count instrument.

Inhibition Assay of Cdk1/Cyclin B1 Activity

Kinase reaction: 1.5 μM histone H1 (Sigma # H-5505) substrate, 25 μM ATP (0.2 μCi $P^{33}$ γ-ATP), 30 ng of baculovirus co-expressed Cdk1/Cyclin B1, suitable concentrations of inhibitor in a final volume of 100 μl buffer (TRIS HCl 10 mM pH 7.5, $MgCl_2$ 10 mM, 7.5 mM DTT+0.2 mg/ml BSA) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and $^{33}P$ labeled histone $H_1$ was detected by radioactivity counting in the Top-Count instrument.

Inhibition Assay Cdk4/Cyclin D1 Activity

Kinase reaction: 0.4 μM mouse GST-Rb (769-921) (# sc-4112 from Santa Cruz) substrate, 10 μM ATP (0.5 μCi $P^{33}$ γ-ATP), 100 ng of baculovirus expressed GST-Cdk4/GST-Cyclin D1, suitable concentrations of inhibitor in a final volume of 50 μl buffer (TRIS HCl 10 mM pH 7.5, $MgCl_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to Multi-Screen plate, to allow substrate binding to phosphocellulose filter. Plates were then washed 3 times with 150 ul/well PBS $Ca^{++}/Mg^{++}$ free and filtered by MultiScreen filtration system.

Detection: filters were allowed to dry at 37° C., then 100 μl/well scintillant were added and $^{33}P$ labeled Rb fragment was detected by radioactivity counting in the Top-Count instrument.

Inhibition Assay of Cdk5/p25 Activity

The inhibition assay of Cdk5/p25 activity was performed according to the following protocol:

Kinase reaction: 1.0 μM biotinylated histone peptide substrate, 0.25 μCi P33g-ATP, 4 nM Cdk5/p25 complex, 0-100 μM inhibitor in a final volume of 100 μl buffer (Hepes 20 mM pH 7.5, $MgCl_2$ 15 mM, 1 mM DTT) were added to each well of a 96 U bottom well plate. After 20 min at 37° C. incubation, the reaction was stopped by the addition of 500 μg SPA beads in phosphate-buffered saline containing 0.1% Triton X-100, 50 μM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100 \times (1 - (\text{Unknown} - \text{Bkgd}) / (\text{Enz. Control} - \text{Bkgd}))$$

$IC_{50}$ values were calculated using a variation of the four parameter logistics equation:

$$Y = 100 / [1 + 10^{((\log EC50 - X)*\text{Slope})}]$$

Where X=log(μM) and Y=% Inhibition.

Inhibition Assay for IGF-1 R Kinase Activity

Specific peptide or protein substrates are trans-phosphorylated by their specific ser-thr or tyr kinase in the presence of ATP traced with $^{33}P$-γ-ATP (gamma phosphate-labeled, Redivue™ Code Number AH9968, 1000-3000 Ci/mmole, Amersham Biosciences Piscataway, N.J. USA), and in the presence of their own optimal buffer and cofactors.

At the end of the phosphorylation reaction, more than 98% cold ATP and radioactive ATP is captured by an excess of the ion exchange dowex resin. The resin then settles down to the bottom of the reaction plate by gravity.

Supernatant is subsequently withdrawn and transferred into a counting plate, then evaluated by β-counting.

Reagents/Assay Conditions i. Dowex Resin Preparation:

500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (with regard to the resin volume) of 150 mM sodium formate buffer are added. The pH is then measured and should be around 3.00.

The washed resin is stable for more than one week; the stock resin is kept at 4° C. before use.

ii. Kinase Buffer (KB):
HEPES 50 mM, pH 7.9
MnCl2 3 mM
DTT 1 mM
NaVO3 3 uM
BSA 0.2 mg/ml iii. Enzyme Pre-Activation:
Prior to start the kinase inhibition assay, IGF-1R is pre-incubated for 30 min at 28° C. in the presence of 100 uM ATP in KB, in a volume equal to 1/60 of the total Enzyme Mix. This will allow the enzyme auto-phosphorylation and full activation.

iiii. Assay Conditions (Final Concentrations):
Enzyme concentration=6 nM
IRS1 substrate=10 uM
ATP=6 uM
$^{33}$P-γ-ATP=1 nM Robotized Dowex Assay The test mix consisted of:
1) 3× Enzyme mix (done in Kinase Buffer 3×), 7 µl /well
2) 3× substrate and ATP mix (done in ddH2O), together with $^{33}$P-γ-ATP, 7 µl/well
3) 3× test compounds (diluted into ddH2O-3% DMSO)-7 µl/well Compound Dilution and Assay Scheme i. Dilution of Compounds:
Test compounds are available as 10 mM solutions in 100% DMSO and distributed into 96 well plates by a dedicated laboratory:
a)—for % inhibition studies, individual dilution plates at 1 mM, 100 uM and 10 uM are prepared in 100% DMSO, then diluted at a 3× concentration (30, 3 and 0.3 uM) in ddH$_2$O, 3% DMSO. A Multimek 96 (Beckman Coulter, Inc.4300 N. Harbor Boulevard, P.O. Box 3100 Fullerton, Calif. 92834-3100 USA) is used for compound pipetting into test plates.
b)—for IC$_{50}$ determination, compounds are diluted to 1 mM in 100% DMSO and plated into the first column of a microtiter plate (A1 to G1), 100 µl.

Well H1 is left empty for the internal standard inhibitor, staurosporine (SIGMA- Aldrich, St. Louis, Mo., USA).

A Biomek 2000 (Beckman Coulter) is used for serial 1:3 dilutions in water, 3% DMSO, from column A1 to A10 and for all the seven compounds in the plate. In a standard experiment, the highest concentration of all compounds is 30 uM, then diluted in the final test mixture down to 10 uM.

Columns 11 and 12 are left available for total activity reference and background evaluation.

ii. Assay Scheme
384-well plates, V bottom (test plates) are prepared with 7 µl of the compound dilution (3×) and then placed onto a PlateTrak 12 robotized station (Perkin Elmer, 45 William Street Wellesley, Mass. 02481-4078, USA); the robot has one 384-tips pipetting head for starting the assay plus one 96-tips head for dispensing the resin) together with one reservoir for the Enzyme mix (3×) and one for the ATP mix (3×).

At the start of the run, the robot aspirates 7 µl of ATP mix, makes an air gap inside the tips (5 µl), and aspirates 7 µl of IGF1R mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 µl of dowex resin suspension into the reaction mix. Three cycles of mixing are done immediately after the addition of the resin.

The resin suspension has to be carefully stirred during the whole step of reaction stop because its settling velocity is extremely high. The resin suspension is very dense. In order to avoid tip clogging, wide bore tips are used to dispense it.

Another mixing cycle is performed after all the plates are stopped, this time using normal tips. The plates are then allowed to rest for about one hour in order to maximize ATP capture. At this point, 20 µl of the supernatant are transferred into 384-Optiplates (Perkin Elmer), with 70 µl of Microscint 40 (Perkin Elmer). After 5 min of orbital shaking, the plates are read on a Perkin-Elmer Top Count radioactivity counter.

iii. Data Analysis
Data were analysed using a customized version of the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted. Compounds showing desired inhibition can be further analysed in order to study the potency of the inhibitor through IC$_{50}$ calculation. In this case, inhibition data obtained using serial dilutions of the inhibitor can be fitted by non-linear regression using the following equation:

$$v = v_0 + \frac{(v_0 - v_b)}{1 + 10^{n(\log IC_{50} - \log[I])}}$$

where vb is the baseline velocity, v is the observed reaction velocity, vo is the velocity in the absence of inhibitors, and [I] is the inhibitor concentration.

Western blot analysis of receptor phosphorylation following stimulation with IGF-1 in MCF-7 human breast cancer cells.

MCF-7 cells (ATCC# HTB-22) were seeded in 12-well tissue culture plates at 2×10^5 cells/well in E-MEM medium (MEM+Earle's BSS+2 mM glutamine+0.1 mM non-essential amino acids)+10% FCS, and incubated overnight at 37° C., 5% CO$_2$, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1131/InsR Tyr 1146 antibody (product #3021, Cell Signaling Technology, Beverly, Mass., USA) for the detection of phosphorylated IGF-1R, or 1/1000 dilution of rabbit IGF-Irβ (H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% $CO_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., Calif., USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed twice with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed twice with PBS, and 40 microL PBS were left in each well for immunofluorescence analysis. Fluorescence images in the DAPI and Cy5™ channels were automatically acquired, stored and analysed using a Cellomics ArrayScan™ IV instrument (Cellomics, Pittsburgh, USA). The Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

Inhibition Assay of Aurora-2 Activity

This in vitro kinase inhibition assay is the same as described for IGF-1R: the principle, the preparation of the Dowex resin, the dilution of test compounds, the robotized assay and the data analysis were exactly the same.

Aurora-2 enzyme does not need any pre-activation.

i. Kinase Buffer (KB) for Aurora-2:
HEPES 50 mM, pH 7.0
$MnCl_2$ 10 mM
DTT 1 mM
$NaVO_3$ 3 uM
BSA 0.2 mg/ml ii. Assay Conditions for Aurora-2 (Final Concentrations)
Enzyme concentration=2.5 nM
Substrate (4× repeats of LRRWSLG)=8 uM
ATP=10 uM
$^{33}P$-γ-ATP=1 nM In Vitro Cell Proliferation Assay The human colon cancer cell line HCT-116 was seeded at 5000 cells/cm$^2$ in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 ul of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:
% of CTR=(Treated−Blank)/(Control−Blank).
$IC_{50}$ values were calculated by LSW/Data Analysis using Microsoft Excel sigmoidal curve fitting.

Given the above assays, the compounds of formula (I) of the invention resulted to possess a remarkable protein kinase inhibitory activity, e.g. Aurora-2 inhibitory activity. See, as an example, the following table I reporting the experimental data of some representative compounds of the invention being tested as Aurora-2 kinase inhibitors ($IC_{50}$ nM) and for their cell antiproliferative effect ($IC_{50}$ nM).

Interestingly, these same derivatives were tested in comparison to a structurally very close compound, herewith defined as Reference compound, which is specifically disclosed in the aforementioned WO04/013146 patent application—see compound No. 421 of example 6.

Inhibition Assay of AKT-1 Activity

Test compounds are prepared as a 10 mM solution in 100% DMSO and distributed into 96 well plates:

i—for % inhibition studies, individual dilution plates at 1 mM, 100 μM and 10 μM are prepared in 100% DMSO, then diluted at a 3× concentration (30, 3 and 0.3 μM) in dd$H_2O$, 3% DMSO. A Multimek 96 (Beckman) is used for compound pipetting into test plates ii—for $IC_{50}$ determination, compounds are diluted to 1 mM in 100% DMSO and plated into the first column of a microtiter plate (A1 to G1), 100 μl. Well H1 is left empty for the internal standard.

A Biomek 2000 (Beckman) is used for serial 1:3 dilutions in water, 3% DMSO, from column A1 to A10 and for all the 7 compounds in the plate. In a standard experiment, the highest concentration of all compounds is 30 μM that is diluted in the final test mixture at 10 μM. Columns 11 and 12 are left available for total activity reference and background evaluation. Assay scheme: U bottom test plates are prepared either with 10 μl of the compound dilution (3×) per well, or 3% DMSO/water, and then placed onto a PlateTrak robotized station (Packard) together with one reservoir for the Enzyme mix (3×) and one for the ATP mix (3×). As the test starts, the robot (PlateTrak system, Perkin Elmer) takes 10 μl of ATP mix, makes an air gap inside the tips (10 μl) and aspirates 10 μl of Enzyme mix. The following dispensation into the plates allows the kinase reaction to start upon 3 cycles of mixing done by the robot itself.

At this point, the correct concentration is restored for all reagents.

The robot incubates the plates for 60 minutes at room temperature, and then stops the reaction by pipetting 150 μl of Dowex resin into the reaction mix. The resin is well stirred before addition to the plates.

The resin is left another 60 minutes to settle down; the robot then takes 50 μl of supernatant from each well and dispenses them into an Optiplate (Packard) with 150 μl of Microscint 40 (Packard).

Counting: Optiplates, covered by a plastic film to avoid radioactive spilling, are then mixed 10 minutes before counting in a Packard Top Count.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) can be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route. For example, a suitable dosage adopted for oral administration of a compound of formula (I) can range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which can be a carrier or a diluent.

The pharmaceutical compositions containing the compounds of the invention are usually prepared following conventional methods and are administered in a suitable pharmaceutical form.

For example, the solid oral forms can contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations can be manufactured in known manner, for example, by means of mixing, granulating, tabletting, sugar-coating, or film-coating processes.

The liquid dispersions for oral administration can be, e.g., syrups, emulsions and suspensions.

As an example, the syrups can contain, as carrier, saccharose or saccharose with glycerine and/or mannitol and sorbitol.

The suspensions and the emulsions can contain, as examples of carriers, natural gum, agar, sodium alginate, pectin, methylcellulose, carboxymethylcellulose, or polyvinyl alcohol.

The suspension or solutions for intramuscular injections can contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions can contain, as a carrier, sterile water or preferably they can be in the form of sterile, aqueous, isotonic, saline solutions or they can contain propylene glycol as a carrier.

The suppositories can contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

General Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 μl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, compounds have been purified by preparative HPLC on a Waters Symmetry C18 (19×50 mm, 5 um) column using a Waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 ml/min.

1H-NMR spectrometry was performed on a Mercury VX 400 operating at 400.45 MHz equipped with a 5 mm double resonance probe [1H (15N-31P) ID_PFG Varian].

The compounds of formula (I), having an asymmetric carbon atom and obtained as racemic mixture, were resolved by HPLC separation on chiral columns. In particular, for example, preparative columns CHIRALPACK® AD can be used.

EXAMPLE 1

2-Bromo-1-pyridin-4-ylethanone hydrobromide

To a stirred solution of 4-acetylpyridine (10 mL, 90 mmol) in glacial acetic acid (40 mL) and 48% hydrobromic acid (15 mL), bromine (4.65 mL, 90 mmol) in glacial acetic acid (10 mL) was added dropwise. After addition, the solution was stirred at room temperature overnight. The white precipitate was filtered off and washed with absolute ethanol, thus obtaining the title compound (22.2 g, 90%) as a white solid containing traces of dibromoderivative, that was used as such in the next step.

$^1$H NMR (DMSO-$d_6$/400 MHz) δ ppm 5.05 (s, 2 H) 8.15 (d, 2 H) 9.0 (d, 2 H).

EXAMPLE 2

2-Bromo-1-(3-fluoropyridin-4-yl)ethanone hydrobromide

Into a stirred solution of 3-fluoropyridine (14 g, 144.2 mmol) in anhydrous THF (150 mL), cooled to −78° C. and under argon, 79.2 mL (158.6 mmol) of a 2N solution of lithiumdiisopropylamide (LDA) in n-heptane, THF, ethylbenzene, were slowly dropped in about 1 h. After stirring for 2.5 h a cooled solution (ca. 0° C.) of acetaldehyde (8.9 mL, 158.5 mmol) in 25 mL of anhydrous THF was slowly dropped and the reaction mixture was stirred at −78° C. for 1.5 h. The solution was warmed to −30° C. and a solution of ammonium chloride (150 g) in 700 mL of water was added. The mixture was extracted with ethylacetate (3×400 mL) and the organic layers were washed with brine (4×200 mL) and dried over sodium sulfate. After concentration, the oil was crystallized with n-hexane (40 mL) and 15.6 g (76% yield) of 1-(3-fluoropyridin-4-yl)ethanol were obtained. A mixture of 1-(3-fluoropyridin-4-yl)ethanol (10 g, 70.3 mmol) and commercial activated $MnO_2$ (8 g, 92.1 mmol) in toluene (100 mL) were refluxed until disappearance of starting material. After cooling, the mixture was filtered on a bed of celite, the cake washed with toluene and the organic phases concentrated to give 3-fluoro-4-acetyl pyridine (6.9 g, 70%) that was used directly in the next step. To a stirred solution of 3-fluoro-4-acetylpyridine (5.3 g, 38.1 mmol) in glacial acetic acid (14 mL) and 48% hydrobromic acid (5.3 mL), bromine (2 mL, 38 mmol) in glacial acetic acid (5.3 mL) was added slowly and dropwise. After addition, the solution was stirred at 60° C. for 2.5 hour. This solution was cooled down and ethylacetate (70 mL) was added. After 30 minutes of stirring, the mixture was filtered and the solid was washed thoroughly with ethylacetate and dried. The title compound was obtained in 82% yield (9.4 g).

$^1$H NMR (DMSO-$d_6$/400 MHz) δ ppm 4.88 (s, 2 H) 7.83 (dd, 1 H) 8.62 (dd, 1 H) 8.81 (d, 1 H).

EXAMPLE 3

1-(2-Aminopyrimidin-4-yl)-2-bromoethanone hydrobromide

A mixture of 3,3-dimethoxy-2-butanone (25 g, 189.2 mmol) and N,N-dimethylformamide dimethylacetal (22.5 g, 189.2 mmol) were stirred at 110° C. for 30 hours and then distilled (115° C., 1 mmHg) thus obtaining 1-(dimethylamino)-4,4-dimethoxypent-1-en-3-one, as a yellow solid (27.3 g, 146 mmol, 77%). Onto a solution of sodium (3.48 g, 151.6 mmol) in anhydrous ethanol (400 mL), solid guanidine hydrochloride (14.5 g, 151.6 mmol) was added at r.t., to give a white suspension into which a solution of 1-(dimethylamino)-4,4-dimethoxypent-1-en-3-one (28.4 g, 151.6 mmol) in anhydrous ethanol (50 mL) was added. The mixture was refluxed for 19 hours. After cooling, the precipitate was filtered and washed with ethanol and with plenty of water, thus obtaining a white solid (8.56 g). The ethanolic solutions were concentrated to dryness, taken up with boiling ethyl acetate (1 L), filtered while hot and then cooled to yield a second crop. Total amount of 4-(1,1-dimethoxyethyl)pyrimidin-2-amine: 17.66 g, 63.5%. A solution of the said amine (17.5 g, 95.5 mmol) in formic acid was stirred at r.t. for 6 hours and concentrated to dryness and the residue was stirred in ethanol (50 mL) and then filtered thus obtaining 1-(2-aminopyrimidin-4-yl)ethanone (9.2 g, 70%). To a solution of 1-(2-aminopyrimidin-4-yl)ethanone (412 mg, 3 mmol) in glacial acetic acid (1 mL) and 48% aq. HBr (0.3 mL), bromine (0.153 mL) in acetic acid (0.4 mL) was added and the resulting orange solution was stirred at room temperature for 15 hours. After diluting with ethyl acetate (15 mL), the precipitate was filtered and washed with ethyl acetate thus affording the title compound as a whitish solid (580 mg, 65%).

$^1$H NMR (DMSO-$d_6$/400 MHz) δ ppm: 4.9 (s, 2 H), 7.0 (d, 2 H), 8.5 (d, 2 H).

EXAMPLE 4

N-(tert-butoxycarbonyl)-DL-aspartic acid

DL aspartic acid acid (1 g) was dissolved in 20 mL of dioxane/water 1:1 and 4.15 mL of triethylamine was added. The mixture was cooled to 0° C. and 2.4 g of di-tert-butyl dicarbonate added. The solution was left at room temperature overnight. The suspension was concentrated and extracted with ethyl acetate and water. The aqueous extract was acidified with 5% aq. $NaHSO_4$ and then extracted with AcOEt three times. The organic extracts were dried over anh. sodium sulfate and the solvent evaporated under vacuum to provide 1.53 g of the title compound.

1H NMR (400 MHz, DMSO-D6) δ ppm 1.36 (s, 9 H) 2.45-2.57 (m, 1 H) 2.60-2.72 (m, 1 H) 4.19-4.31 (m, 1 H) 7.01 (d, J=8.50 Hz, 1 H) 12.45 (bs, 2 H).

EXAMPLE 5

DL-(2.5-dioxo-tetrahydro-furan-3-yl)-carbamic acid tert-butyl ester

A mixture of 1 g (4.29 mmol) of N-(tert-butoxycarbonyl)-DL-aspartic acid and 0.98 g (5.15 mmol) of 1-(3-dimethylaminopropyl)-3-ethylcarbodiimide hydrochloride (EDCI) in 100 mL of DCM, was stirred at room temperature overnight. The solution was extracted three times with 5% aq. $NaHSO_4$, the organic extracts were dried over anh. sodium sulfate and the solvent evaporated under vacuum. In this way 750 mg of the title compound were recovered. 1H NMR (400 MHz, DMSO-D6) δ ppm 1.38 (s, 9 H) 2.78-2.90 (m, 1 H) 3.15-3.28 (m, 1 H) 4.54-4.65 (m, 1 H) 7.73 (d, J=7.91 Hz, 1 H).

EXAMPLE 6

DL-3-tert-butoxycarbonylamino hydroxy-butyric acid

To a solution of 192 mg of sodium borohydride in 15 mL of anhydrous THF, cooled at 0° C., 1 g of DL-(2,5-dioxo-tetrahydro-furan-3-yl)-carbamic acid tert-butyl ester, dissolved in 15 mL of anhydrous THF, was added dropwise and stirring was maintained for 4 hours at 0° C.

The solution was acidified with 5% aq. $NaHSO_4$, and concentrated. The product was extracted with AcOEt three times. The combined organic phases were dried over anh. sodium sulfate and concentrated under vacuum to yield 700 mg of the title compound.

1H NMR (400 MHz, DMSO-D6) δ ppm 1.37 (s, 9 H) 2.14-2.29 (m, 1 H) 2.36-2.48 (m, 1 H) 3.13-3.40 (m, 2 H) 3.65-3.81 (m, 1 H) 4.69 (bs, 1 H) 6.47-6.60 (d, J=8.21 Hz, 1 H) 11.99-12.18 (bs, 1 H).

EXAMPLE 7

DL-3-tert-butoxycarbonylamino-4-(tert-butyl-dimethyl-silanyloxy)-butyric acid

To a solution of 1 g of DL-3-tert-butoxycarbonylamino-4-hydroxy-butyric acid in a mixture of DMF/DCM 1:5, 1.24 g of imidazole and 1.7 g of tert-butyldimethylsilyl chloride were added. The solution was left stirring at room temperature overnight. The solution was extracted three times with 5% aq. $NaHSO_4$ and the aqueous phases were washed twice with DCM. The organic extracts were dried over anh. sodium sulfate and the solvent evaporated under vacuum to provide 2.1 g of the title compound.

$[M+H]^+$=334; $[M-H]^-$=332

EXAMPLE 8

DL-2-tert-butoxycarbonylamino-succinic acid 4-methyl ester

To a stirred solution of DL-2-amino-succinic acid 4-methyl ester in dioxane/$H_2O$ (2:1, 110 mL) $Na_2CO_3$ (3.92 g, 0.037 mol) was added. When evolution of $CO_2$ ceased, more $Na_2CO_3$ (3.92 g, 0.037 mol) was added, followed by addition of $Boc_2O$ (8.87 g, 0.04 mol) and the reaction mixture was stirred at 0° C. for 1 h (a white precipitate formed within 30 minutes) and at room temperature overnight. The solvent was removed and the residue was washed with $Et_2O$. The aqueous solution was acidified with sat. aq. $NaHSO_4$ and extracted with $Et_2O$. The organic phase was dried over anh. $Na_2SO_4$ and evaporated to afford the title compound as a white solid (6.7 g, 74%).

$[M+H]^+$=248; $[M-H]^-$=246

EXAMPLE 9

DL-3-tert-butoxycarbonylamino-4-hydroxy-butyric acid methyl ester

To a solution of DL-2-tert-butoxycarbonylamino-succinic acid 4-methyl ester (5 g, 0.02 mol) in dry THF (100 mL) at −10° C. $Et_3N$ (3.1 mL, 0.022 mol) was added, followed by ethyl chloroformate (2.1 mL, 0.022 mol). After 10 min, $NaBH_4$ (2.27 g, 0.06 mol) was added and then MeOH was dropped into the mixture over a period of 20 min at 0° C. The reaction mixture was stirred for 1 hour at 0° C. and for 2 hours at room temperature then neutralized with sat. aq. $NaHSO_4$. The organic solvent was removed and the product was extracted with AcOEt three times. The combined organic phases were washed consecutively with sat. aq. $NaHSO_4$, water, sat. aq. $NaHCO_3$, water and dried over anh. $Na_2SO_4$. The solvent was evaporated and the residue was purified by flash chromatography (n-hexane/AcOEt 5:1), affording the title compound (1.63 g, 35%).

$[M+H]^+$=234

EXAMPLE 10

DL-4-azido-3-tert-butoxycarbonylamino-butyric acid methyl ester

To a stirred solution of DL-3-tert-butoxycarbonylamino-4-hydroxy-butyric acid methyl ester (700 mg, 3 mmol) in $CH_2Cl_2$ (10 mL), $Et_3N$ (0.626 mL, 4.5 mmol) and methanesulfonyl chloride (0.350 mL, 4.5 mmol) were added at 0° C. The reaction mixture was stirred at 0° C. for 30 minutes and at room temperature for 2 h. The organic phase was washed with brine, sat. aq. $NaHSO_4$, sat. aq. $NaHCO_3$ and brine and dried and the solvent was removed to give the corresponding mesylate (712 mg, 76%).

The mesylate was dissolved in DMF (10 mL). Sodium azide (585 mg, 9 mmol) was added and the mixture was heated at 60° C. for 6 h. The solvent was removed and the residue was taken up in AcOEt. The organic phase was washed with brine, dried and evaporated to give 450 mg of the title compound (76%).

1H NMR (400 MHz, DMSO-D6) δ ppm 1.38 (s, 9 H) 2.40-2.58 (m, 2 H) 3.3 (bs, 2 H) 3.6 (s, 3 H) 3.9 (m, 1 H) 7.01 (d, J=8.3 Hz, 1 H).

EXAMPLE 11

DL-4-azido-3-tert-butoxycarbonylamino-butyric acid

DL-4-azido-3-tert-butoxycarbonylamino-butyric acid methyl ester (450 mg, 1.74 mmol) was dissolved in THF (12 mL) and hydrolized by adding an aqueous solution of LiOH (393 mg).

1H NMR (400 MHz, DMSO-D6) δ ppm 1.4 (s, 9 H) 2.40 (d, 2 H, J=6.8 Hz) 3.3 (bs, 2 H) 3.9 (m, 1 H) 7.01 (d, J=8.3 Hz, 1 H) 12.3 (s, 1 H).

EXAMPLE 12

DL-2-(tert-butyl-dimethyl-silanyloxymethyl)-4,6-dioxo-piperidine-1-carboxylic acid tert-butyl ester To a solution of 2 g of DL-3-tert-butoxycarbonylamino-4-(tert-butyl-dimethyl-silanyloxy)-butyric acid in 70 mL of DCM, 1 g of Meldrum's acid and 1.1 g of 4-dimethylaminopyridine were added. The solution was cooled to 0° C. and 1.37 g of EDCI, dissolved in 30 mL of DCM, were added dropwise. Stirring was maintained for 3 hours then the solution was extracted three times with 5% aq. $NaHSO_4$. The organic extracts were dried over anh. sodium sulfate and the solvent evaporated under vacuum. The solid was dissolved in 200 mL of ethyl acetate, refluxed for 4 hours, then concentrated to dryness. The raw product was purified by flash chromatography over silica gel thus providing 510 mg of the title compound as an oil.

HPLC r.t. 6.42 $[M+H^+]$=358; $[M-H]^-$=356

¹H NMR (DMSO-d₆/400 MHz) δ ppm: −0.09--0.07 (6H), 0.76-0.92 (9H), 1.44 (9H), 2,52 (m, 1H), 2.81 (m,1H), 3.3 (2H), 3.7 (m, 2H), 4.27 (m, 1H).

By working in an analogous way, as in Example 12, and optionally removing the tert-butoxycarbonyl protecting group by treatment with trifluoroacetic acid at room temperature, the following compounds in Examples 13-15 were prepared.

EXAMPLE 13

(R)-6-benzyloxymethyl-piperidine-2,4-dione

Starting from Boc-O-benzyl-L-beta-homoserine.
¹H NMR (DMSO-d₆/400 MHz) δ ppm: 2.4 (dd, 1H), 2.7 (dd, 1H), 3.01-3.17 (dd, 2H), 3.48 (s, 2H), 3.77 (m, 1H), 4.46 (s, 2H), 7.28 (m, 2H), 7.33 (m, 3H), 8.06 (bs, 1H).
[M+H]⁺=234

EXAMPLE 14

DL-2-(3-benzyloxycarbonylamino-propyl)-4,6-di-oxo-piperidine-1-carboxylic acid tert-butyl ester Starting from Boc-β-LYS(Z)-OH dicyclohexylamine.
ESI (+) MS: m/z 405 (MH⁺).

EXAMPLE 15

DL-6-azidomethyl-piperidine-2,4-dione

Starting from DL-4-azido-3-tert-butoxycarbonylaminobutyric acid.
¹H NMR (DMSO-d₆/400 MHz) δ ppm: 2.3 (m, 2H), 3.11 (m, 3H), 3.85 (m, 2H), 9.5 (s, 1H).

EXAMPLE 16

5-(3-Benzyloxy-propyl)-piperidine-2,4-dione

To a solution of tert-butyl 2,4-dioxopiperidine-1-carboxylate (3.84 g, 18 mmol) in anhydrous THF (100 mL), cooled at −20° C. under nitrogen atmosphere, 1M LiHMDS in THF (54 mL) was added dropwise. After 20 min under stirring, (3-bromo-propoxymethyl)-benzene (54 mmol) was added and the solution was stirred at −20° C. for 2 hours. The reaction mixture was poured into 5% aq. KHSO₄ and extracted with DCM two times. The collected organic layers were concentrated to 500 mL and 50 mL of TFA were added. The resulting solution was stirred at room temperature for 1 hour. After evaporation, the residue was purified by column chromatography (hexane/EtOAc 1:2) affording 3.85 g of the title compound (14.7 mmol, 82%).
1H NMR (400 MHz, DMSO-D6) δ ppm 1.35 (m, 1H), 1.58 (m, 2H), 1.74 (m, 1H), 2.50 (m, 1H), 3.00-3.33 (m, 4H), 3.43 (t, 2H), 4.45 (s, 2H), 7.20-7.40 (m, 5H), 8.04 (s, 1H).
ESI (+) MS: m/z 262 (MH⁺).

By working in an analogous way, as in Example 16, from the suitable alkyl halide, the following compounds in Examples 17-19 were prepared.

EXAMPLE 17

5-(2-Benzyloxy-ethyl)-piperidine-2,4-dione

1H NMR (44 MHz, DMSO-D6) δ ppm 1.60 (m, 1H), 1.97 (m, 1H), 2.59 (m, 1H), 3.15 (m, 1H), 3.40 (m, 1H), 3.51 (m, 2H), 4.46 (s, 2H), 7.33 (m, 6H), 8.06 (m, 2H).
ESI (+) MS: m/z 248 (MH*).

EXAMPLE 18

5-)3.3.3-Trifluoro-propyl)-piperidine-2,4dione and 5-(3.3-diflouro-ally)-piperidine-2.4 dione From 1,,1-trifluoro-3-iodo-propane.
ESI (+) MS:/m/z 210 (MH⁺)
ESI (+) MS:/m/z 190 (MH⁺)

EXAMPLE 19

5-(2-Fluoro-ethyl)-piperidine-2,4-dione

From 1-fluoro-2-bromo-ethane.
1H NMR (400 MHz, DMSO-D6) δ ppm 1.65 (m, 1H), 2.07 (m, 1H), 2.63 (m, 1H), 3.15-3.43 (m, 4H), 4.48 (m, 1H), 4.52 (m, 1H), 8.08 (s, 1H)
ESI (+) MS: m/z 160 (MH⁺).

EXAMPLE 20

DL-6-(3-benzyloxycarbonylamino-propyl)-4-oxo-2-pyridin-4-yl-1,4,6,7-tetrahydro-pyrrolo[3,2-c]pyridine-5-carboxylic acid tert-butyl ester To a suspension of 2-bromo-1-pyridin-4-ylethanone hydrobromide (0.76 g, 2.59 mmol) and DL-2-(3-benzyloxycarbonylamino-propyl)-4,6-dioxo-piperidine-1-carboxylic acid tert-butyl ester (1.05 g, 2.59 mmol) in absolute EtOH (40 mL), ammonium acetate (0.81 g, 10.8 mmol) was added and the deep red solution was stirred at room temperature for 18 h. After solvent removal, the residue was treated with ethyl acetate/abs. Ethanol 15:1 (50 mL), the precipitate was filtered off and the obtained solution was charged on flash silica gel and eluted with ethyl acetate/abs. Ethanol 15:1. In this way the title compound was obtained as a yellowish solid (0.4 g, 30% yield).
ESI (+) MS: m/z 505 (MH⁺)

By working in an analogous way, as in Example 19, the following compounds in Examples 21-32 were also obtained:

EXAMPLE 21

®6-benzyloxymethyl-2-pyridinyl-1,5,6,7-tetrahydro-pyrrolo[3,2-c]pyridin-4-one

¹H NMR (DMSO-d₆/400 MHz) δ ppm: 2.91 (dd, 1 H), 3.01 (dd, 1 H), 3.51 (m, 2H), 3.87 (m, 1H), 4.53 (s, 2H), 6.96 (s, br, 1H), 7.01 (s, 1H), 7.34 (m, 5H), 7.61 (d, 2H), 8.49 (d, 2H), 11.91 (bs, 1H).
[M+H]⁺=334

EXAMPLE 22

DL-7-(2-fluoro-ethyl)-2-pyridin-4-yl-1,5,6,7-tetrahydro-pyrrolo[3,2-c]pyridin-4-one 1H NMR (400 MHz, DMSO-D6) δ ppm 1.92 (m, 1H), 2.19 (m, 1H), 3.10 (m, 1H), 3.26 (m, 1H), 3.53 (m, 1H), 4.54 (m, 1H), 4.63 (m, 1H), 7.01 (s, 1H), 7.07 (s, 1H), 7.65 (d, 2H), 8.49 (d, 2H), 11.80 (s, 1H).
ESI (+) MS: m/z 260 (MH⁺).

The racemic (7R,7S) mixture was separated by chiral column chromatography, according to conventional methods, by using a CHIRALPACK AD® column and eluting with n-hexane/i-propanol/methanol=55:35:10, so as to afford the desired (7R) and (7S) enantiomers, the absolute stereochemistry of which was not determined:

EXAMPLE 23

(R) and (S)-7-(2-fluoro-ethyl)-2-pyridin-4-yl-1,5,6,7-tetrahydro-pyrrolo[3,2-c]pyridin-4-one hydrochloride First eluted peak) 1H NMR (400 MHz, DMSO-D6) δ ppm 2.05 (m, 1H), 2.24 (m, 1H), 3.15 (m, 1H), 3.30 (m, 1H), 3.60 (m, 1H), 4.56 (m, 1H), 4.68 (m, 1H), 7.31 (s, 1H), 7.59 (s, 1H), 8.26 (d, 2H), 8.72 (d, 2H), 12.53 (s, 1H).
ESI (+) MS: m/z 260 (MH$^+$).
Second eluted peak) 1H NMR (400 MHz, DMSO-D6) δ ppm 2.08 (m, 1H), 2.24 (m, 1H), 3.15 (m, 1H), 3.30 (m, 1H), 3.60 (m, 1H), 4.56 (m,1H), 4.68 (m, 1H), 7.31 (s, 1H), 7.59 (s, 1H), 8.26 (d, 2H), 8.72 (d, 2H), 12.53 (s, 1H).
ESI (+) MS: m/z 260 (MH$^+$).

EXAMPLE 24

DL-6-(tert-butyl-dimethyl-silanyloxymethyl)-4-oxo-2-pyridinyl-1,4,6,7-tetrahydro-pyrrolo[3,2-c]pyridine-5-carboxylic acid tert-butyl ester HPLC r.t. 6.76 [M+H]$^+$=458; [M-H]$^-$=456

EXAMPLE 25

6-Azidomethyl-2-pyridin-4-yl-1,5,6,7-tetrahydro-pyrrolo[3,2-c]pyridin-4-one $^1$H NMR (DMSO-d$_6$/400 MHz) δ ppm: 2.87 (dd, 1H), 3.02 (dd, 1H), 3.50 (dd, 1H), 3.57 (dd, 1H), 3.83 (m, 1H), 7.02 (s, 1H), 7.20 (s, 1H), 7.62 (d, 2H), 8.49 (d, 2H), 11.95 (bs, 1H). [M+H]$^+$=269

By working in an analogous way and starting from 1-(2-aminopyrimidin-4-yl)-2-bromoethanone hydrobromide the following compounds were also obtained:

EXAMPLE 26

(R)-2-(2-Amino-pyrimidin-4-yl)-6-benzyloxymethyl-1,5,6,7-tetrahydro-pyrrolo[3,2-c]pyridin-4-one $^1$H NMR (DMSO-d$_6$/400 MHz) δ ppm: 2.88 (dd,1H), 2.97 (dd, 1H), 3.46 (m, 2H), 3.82 (m, 1H), 4.49 (s, 2H), 6.28 (bs, 2H), 6.87 (d, 1H), 6.94 (bs, 1H), 6.99 (s, 1H), 7.32 (m, 5H), 8.13 (d, 1H), 11.74 (bs, 1H).
[M+H]$^+$=350

EXAMPLE 27

DL-2-(2-Amino-pyrimidin-4-yl)-7-(2-benzyloxypropyl)-1,5,6,7-tetrahydro-pyrrolo[3,2-c]pyridin-4-one 1H NMR (400 MHz, DMSO-D6) δ ppm 1.70 (m, 4H), 2.92 (m, 1H), 3.19 (m, 1H), 3.42 (m, 2H), 3.49(m, 1H), 4.43 (s, 2H), 6.29 (s, 2H), 6.90 (d, 1H), 6.98 (s, 1H), 7.01 (s, 1H), 7.20-7.35 (m, 5H), 8.13 (d, 1H), 11.62 (s, 1H).
ESI (+) MS: m/z 378 (MH$^+$).

EXAMPLE 28

DL-2-(2-amino-pyrimidin-4-yl)-7-(2-hydroxy-ethyl)-1,5,6,7-tetrahydro-pyrrolo[3,2-c]pyridin-4-one $^1$H NMR (400 MHz, DMSO-D6) δ ppm 1.80 (m, 1H), 2.07 (m, 1H), 3.07 (m, 1H), 3.24 (m, 1H), 3.47 (m, 1H), 3.55 (m, 2H), 4.50 (m, 2H), 6.30 (s, 2H), 6.91 (d, 1H), 7.01 (s, 1H), 7.03 (s,1H), 7.25-7.35 (m, 5H), 8.14 (d, 1H), 11.60 (s, 1H).
ESI (+) MS: m/z 364 (MH$^+$).

EXAMPLE 29

DL-2-(2-amino-pyrimidin-4-yl)-7-(2-fluoro-ethyl)-1,5,6,7-tetrahydro-pyrolo[3,2-c]pyridin-4-one 1H NMR (400 MHz, DMSO-D6) δ ppm 1.92 (m, 1H), 2.15 (m, 1H), 3.11 (m, 1H), 3.32 (m, 1H), 3.52 (dd,1H), 4.52 (t, 1H), 4.64 (t, 1H), 6.33 (s, 2H), 6.94 (d,1H), 7.04 (s, 1H), 7.07 (s, 1H) 8.17 (d, 1H), 11.68 (s, 1H).

The racemic (7R,7S) mixture was separated by chiral column chromatography, according to conventional methods, by using a CHIRALCELL OJ® column and eluting with n-hexane/ethanol/methanol=60:35:5, so as to afford the desired (7R) and (7S) enantiomers, the absolute stereochemistry of which was not determined:

EXAMPLE 30

(R) and (S)-2-(2-amino-pyrimidin-4-yl)-7-(2-fluoro-ethyl)-1,5,6,7-tetrahydro-pyrrolo[3,2-c]pyridin-4-one hydrochloride First eluted peak) ee 99%
Second eluted peak) ee 96%

EXAMPLE 31

DL-2-(2-amino-pyrimidin-4-yl)-7-(3,3,3-trifluoro-propyl)-1,5,6,7-tetrahydro-pyrrolo[3,2-c]pyridin-4-one hydrochloride 1H NMR (400 MHz, DMSO-D6) δ ppm 1.81 (m,1H), 2.01 (m, 1H), 2.27 (m,1H), 2.41 (m, 1H), 3.12 (m, 1H), 3.42 (m, 2H), 7.30 (s, 1H), 7.35 (d, 1H), 7.51 (s, 1H), 7.97 (s, 2H), 8.24 (d, 1H), 12.33 (s, 1H).
ESI (+) MS: m/z 326 (MH$^+$).

The racemic (7R,7S) mixture was separated by chiral column chromatography, according to conventional methods, by using a CHIRALCELL OD® column and eluting with n-hexane/ethanol=75:25, so as to afford the desired (7R) and (7S) enantiomers, the absolute stereochemistry of which was not determined:

EXAMPLE 32

(R) and (S)-2-(2-amino-pyrimidin-4-yl)-7-(3,3,3-trifluoro-propyl)-1,5,6,7-tetrahydro-pyrrolo[3,2-c]pyridin-4-one hydrochloride First eluted peak) ee 99%
Second eluted peak) ee 98%

EXAMPLE 33

DL-2-(2-amino-pyrimidin-4-yl)-7-(3,3-difluoro-allyl)-1,5,6,7-tetrahydro-pyrrolo[3,2-c]pyridin-4-one hydrochloride 1H NMR (400 MHz, DMSO-D6) δ ppm 2.32 (m, 1H), 2.40 (m, 1H), 3.11 (m, 1H), 3.58 (m, 2H), 4.55 (m, 1H), 7.29 (s, 1H), 7.34 (d, 1H), 7.51 (s, 1H), 8.01 (s, 2H), 8.24 (d, 1H), 12.34 (s, 1H).

ESI (+) MS: m/z 306 (MH$^+$).

EXAMPLE 34

DL-6-(3-amino-propyl)-2-pyridin-4-yl-1,5,6,7-tetrahydro-pyrrolo[3,2-c]pyridin-4-one DL-6-(3-benzyloxycarbonylamino-propyl)-4-oxo-2-pyridin-4-yl-1,4,6,7-tetrahydro-pyrrolo[3,2-c]pyridine-5-carboxylic acid tert-butyl ester (0.4 g) was dissolved in cyclohexene (10 mL) and absolute EtOH (20 mL), 10% Pd on carbon (0.2 g) was added and the mixture was refluxed for 1.5 hours. After filtration through celite and solvent evaporation under reduced pressure, the compound was treated with 4N HCl in dioxane (20 mL) for 2.5 hours at room temperature. The solution was concentrated and the residue treated with ethyl acetate. The precipitate was filtered, washed with little ethyl acetate and dried. The residue was dissolved in 4M HCl in dioxane and stirred for 4 hours at room temperature. The solution was concentrated and the title compound, as the dihydrochloride, was recovered as a yellowish solid (0.29 g, quantitative).

1H NMR (400 MHz, DMSO-D6) δ ppm 1.57-1.71 (m, 4 H) 2.71-2.77 (m, 1 H) 2.78-2.84 (m, 2 H) 3.05-3.11 (m, 1 H) 3.67-3.78 (m, 1 H) 7.35 (d, J=1.59 Hz, 1 H) 7.57 (d, J=2.32 Hz, 1 H) 7.85 (s, 3 H) 8.23 (d, J=7.07 Hz, 2 H) 8.70 (d, J=7.07 Hz, 2 H) 12.94 (s, 1 H).

ESI (+) MS: m/z 271 (MH$^+$).

By working in an analogous way, as in Example 34, the following compound in Example 35 was also obtained:

EXAMPLE 35

DL-2-(2-amino-pyrimidin-4-yl)-7-(3-hydroxy-propyl)-1,5,6,7-tetrahydro-pyrrol[3,2-c]pyridin-4-one 1H NMR (400 MHz, DMSO-D6) δ ppm 1.40 (m, 1H), 1.54 (m, 2H), 1.65 (m, 1H), 2.91 (m, 1H), 3.18 (m, 1H), 3.40 (m, 2H), 3.48 (m, 1H), 4.44 (t, 1H), 6.30 (s, 2H), 6.91 (d, 1H), 6.99 (s, 1H), 7.02 (s, 1H), 8.13 (d, 1H), 11.62 (s, 1H).

ESI (+) MS: 288 m/z (MH$^+$).

EXAMPLE 36

DL-2-(2-Amino-pyrimidin-4-yl)-7-(2-hydroxy-ethyl)-1,5,6,7-tetrahydro-pyrrolo[3,2-c]pyridin-4-one $^1$H NMR (400 MHz, DMSO-D6) δ ppm 1.69 (m, 1H), 1.84 (m, 1H), 3.05 (m, 1H), 3.21 (m, 1H), 3.51 (m, 1H, 4.79 (t, 2H), 6.31 (s, 2H), 6.92 (d, 1H), 7.01 (s, 1H), 7.03 (s, 1H), 8.15 (d, 1H), 11.60 (s, 1H).

ESI (+) MS: m/z 274 (MH$^+$).

EXAMPLE 37

(R)(-2-(2-amino-pyrimidin-4-yl)-6-benzyloxymethyl-1-(2,2,2-trifluoro-ethyl)-1,5,6,7-tetrahydro-pyrrolo[3,2-c]pyridin-4-one To a stirred mixture of (R)-2-(2-amino-pyrimidin-4-yl)-6-benzyloxymethyl-1,5,6,7-tetrahydro-pyrrolo[3,2-c]pyridin-4-one (73 mg, 0.21 mmol) in dry DMF (2 mL) were added 18-crown-6 ether (110.5 mg, 0.42 mmol), K$_2$CO$_3$ (115.5 mg, 0.84 mmol) and CF$_3$CH$_2$OSO$_2$CF$_3$ (0.21 mmol). The reaction mixture was heated at 50° C. for 7 hours, then treated with water and extracted with AcOEt. The organic phase was dried over anh. Na$_2$SO$_4$ and evaporated to yield a crude product that was purified by flash chromatography (eluant: DCM/MeOH 95:5) to provide 64 mg of the title product.

$^1$H NMR (DMSO-d$_6$/400 MHz) δ ppm: 2.94 (dd, 1H), 3.08 (dd, 1H), 3.5 (m, 2H), 3.87 (m, 1H), 4.51 (s, 2H), 5.75 (m, 1H), 6.01 (m, 1H) 6.64 (bs, 2H), 6.91 (d, 1H, 7.10 (s, 1H), 7.21 (s, 1H), 7.3 (m, 5H), 8.14 (d, 1H).

[M+H]$^+$=432

EXAMPLE 38

DL-6-hydroxymethyl-2-pyridin-4-yl-1,5,6,7-tetrahydro-pyrrolo[3,2-c]pyridin-4-one hydrochloride A solution of 50 mg of DL-6-(tert-butyl-dimethyl-silanyloxymethyl)-4-oxo-2-pyridin-4-yl 1,4,6,7-tetrahydro-pyrrolo[3,2-c]pyridine-5-carboxylic acid tert-butyl ester in 5 mL of 4M HCl in dioxane was stirred for 4 hours at room temperature. The solution was concentrated and the title compound recovered.

1H NMR (400 MHz, DMSO-D6) δ ppm 2.92 (dd, J=16.83, 7.68 Hz, 2 H) 3.03 (dd, J=16.95, 5.98 Hz, 1 H) 3.46-3.54 (m, 2 H) 3.65-3.71 (m, 1 H) 7.12 (s, 1 H) 7.57 (d, J=2.44 Hz, 1 H) 8.17 (d, J=6.95 Hz, 2 H) 8.70 (d, J=7.07 Hz, 2 H) 12.65 (bs, 1 H).

EXAMPLE 39

DL-6-(3-benzylamino-proyl)-2-pyridin-4-yl-1,5,6,7-tetrahydro-pyrrolo[3,2-c]pyridin-4-one and DL-6-(3-dibenzylamino-propyl)-2-pyridin-4-yl-1,5,6,7-tetrahydro-pyrrolo[3,2-c]pyridin-4-one To a solution of DL-6-(3-amino-propyl)-4-oxo-2-pyridin-4-yl-1,4,6,7-tetrahydro-pyrrolo[3,2-c]pyridine-5-carboxylic acid tert-butyl ester (0.1 g, 0.296 mmol) in anhydrous DMF (3 mL), under argon and cooling at 0° C., trifluoroacetic acid (0.25 mL, 3.2 mmol) and freshly distilled benzaldehyde (0.055 mL, 0.539 mmol) were added. Sodium triacetoxy borohydride (0.17 g, 0.81 mmol) was added and the clear yellow solution was stirred at room temperature for 60 hours. The reaction mixture was poured into water, extracted with ethyl acetate, dried and charged on flash silica gel, eluting first with DCM/methanol 15:1 to collect DL-6-(3-dibenzylamino-propyl)-4-oxo-2-pyridin-4-yl-1,4,6,7-tetrahydro-pyrrolo[3,2-c]pyridine-5-carboxylic acid tert-butyl ester (0.035 g, 0.063 mmol, 21%) and then with DCM/methanol/30% aq. ammonia 15:10:0.2, to collect DL-6-(3-benzylamino-propyl)-4-oxo-2-pyridin-4-yl-1,4,6,7-tetrahydro-pyrrolo[3,2-c]pyridine-5-carboxylic acid tert-butyl ester (0.03 g, 0.065 mmol, 22%). The two compounds were separately dissolved in methanol (2 mL) and treated with 4 N HCl in dioxane (2 mL) for 2.5 hours at room temperature. The solution was concentrated and the residue treated with ethyl acetate. The precipitate was filtered, washed with little ethyl acetate and dried. Obtained was DL-6-(3-dibenzylamino-propyl)-2-pyridin-4-yl-1,5,6,7-tetrahydro-pyrrolo[3,2-c]pyridin-4-one, as the dihydrochloride, and DL-6-(3-benzylamino-propyl)-2-pyridin-4-yl-1,5,6,7-tetrahydro-pyrrolo[3,2-c]pyridin-4-one, as the dihydrochloride.

1H NMR (400 MHz, DMSO-D6) δ ppm 1.43-1.55 (m, 2 H) 1.77-2.06 (m, 2 H) 2.64-3.10 (m, 4 H) 3.60-3.73 (m, 1 H) 4.34 (s, 4 H) 7.33 (s, 1 H) 7.41-7.67 (m, 10 H) 8.23 (d, J=6.83 Hz, 2 H) 8.70 (d, J=6.95 Hz, 2 H) 12.88 (s, 1 H).

ESI (+) MS: m/z 451 (MH$^+$).

$^1$H NMR (400 MHz, DMSO-D6) δ ppm 1.56-1.82 (m, 4 H) 2.78 (dd, J=16.71, 8.54 Hz, 1 H) 2.87-2.97 (m, 2 H) 3.06 (dd, J=16.34, 5.49 Hz, 1 H) 3.67-3.77 (m, 1 H) 4.14 (t, J=5.61 Hz, 2 H) 7.34 (s, 1 H) 7.39-7.59 (m, J=48.90 Hz, 5 H) 8.22 (d, J=6.83 Hz, 2 H) 8.70 (d, J=7.07 Hz, 2 H) 9.11 (s, 2 H).

ESI (+) MS: m/z 361 (MH$^+$).

EXAMPLE 40

DL-6-(3-isobutylamino-propyl)-2-pyridin-4-yl-1,5,6,7-tetrahydro-pyrrolo[3,2-c]pyridin-4-one To a solution of DL-6-(3-amino-propyl)-4-oxo-2-pyridin-4-yl-1,4,6,7-tetrahydro-pyrrolo[3,2-c]pyridine-5-carboxylic acid tert-butyl ester (0.1 g, 0.296 mmol) in methanol (3 mL), 2-methyl-propionaldehyde (0.023 mL, 0.25 mmol) and sodium cyanoborohydride (0.03 g, 0.49 mmol) were added and the solution was stirred at room temperature for 4 hours. The solvent was removed, water was added, the crude product was extracted twice with ethyl acetate and dried over anh. sodium sulphate. The residue was purified by flash chromatography eluting with DCM/methanol 15:2 and then with DCM/methanol/30% aq. ammonia 15:2:0.1. The protected compound (0.045 g, 0.097 mmol, 40%) was dissolved in methanol (2.5 mL) and treated with 4 N HCl in dioxane (1 mL) for 2.5 hours at room temperature. The solution was concentrated and the residue treated with ethyl acetate. The yellow precipitate of the title compound, as the dihydrochloride, was filtered, washed with little ethyl acetate and dried.

1H NMR (400 MHz, DMSO-D6) δ ppm 0.97 (d, J=6.71 Hz, 6 H) 1.56-1.68 (m, 2 H) 1.69 -1.81 (m, 2 H) 1.90-2.05 (m, 1 H) 2.70-2.81 (m, 4 H) 2.84-2.97 (m, 2 H) 3.07 (dd, J=16.58, 5.61 Hz, 2 H) 3.67-3.79 (m, 1 H) 7.35 (s, 1 H) 7.57 (d, J=2.32 Hz, 1 H) 8.21 (d, J=5.49 Hz, 2 H) 8.69 (d, J=6.95 Hz, 2 H) 12.89 (s, 1 H).

ESI (+) MS: m/z 327(MH$^+$).

By working in an analogous way, as in Example 40, using 4 equivalents of 2-methyl-propionaldehyde and a reaction time of 18 hours, the following compound in Example 41 was also obtained, as the dihydrochloride, in 63% yield:

EXAMPLE 41

DL-6-(3-diisobutylamino-propyl)-2-pyridin-4-yl-1,5,6,7-tetrahydro-pyrrol[r3,2-c]pyridin-4-one 1H NMR (400 MHz, DMSO-D6) δ ppm 0.97-1.04 (m, 12 H) 2.48-2.55 (m, 14 H) 3.70-3.80 (m, 1 H) 7.38 (s, 1 H) 7.54-7.57 (m, 1 H) 8.22 (d, J=6.58 Hz, 2 H) 8.70 (d, J=6.95 Hz, 2 H) 12.93 (s, 1 H).

ESI (+) MS: m/z 383 (MH$^+$).

EXAMPLE 42

(4-Oxo-2-pyridin-4-yl-4,5,6,7-tetrahydro-1H-pyrrolo[3,2-c]pyridin-6-ylmethyl)-carbamic acid tert-butyl ester A solution of Me$_3$P in THF (1M, 0.15 mmol, 0.150 mL) was added to a stirred mixture of 6-azidomethyl-2-pyridin-4-yl-1,5,6,7-tetrahydro-pyrrolo[3,2-c]pyridin-4-one (0.075 mmol, 20 mg) in THF (1 mL) and NaOH (1M, 0.165 mmol, 0.165 mL) at r.t.; a solution of Boc$_2$O (0.165 mmol, 36 mg) in THF/H$_2$O (1 mL) was then added. After 2 days the mixture was quenched by addition of a phosphate buffer solution (pH7). Extraction with CH$_2$Cl$_2$, drying of the organic extracts, removal of the solvent and titration with CH$_2$Cl$_2$/hexane afforded the title compound, 16 mg.

$^1$H NMR (DMSO-d$_6$/400 MHz) δ ppm: 1.41 (9H), 2.74 (dd, 1H), 2.91 (dd, 1H), 3.13 (m, 2H), 3.68 (m, 1H), 6.93 (s, 1H), 7.01 (2H), 7.62 (d, 2H), 8.49 (br, 2H), 11.90 (s br, 1H).

[M+H]$^+$=343

EXAMPLE 43

6-Aminomethyl-2-pyridin-4-yl-1,5,6,7-tetrahydro-pyrrolo[3,2-c]pyridin-4-one bis-trifluoroacetate.

To a stirred mixture of (4-oxo-2-pyridin-4-yl-4,5,6,7-tetrahydro-1H-pyrrolo[3,2-c]pyridin-6-ylmethyl)-carbamic acid tert-butyl ester (0.046 mmol, 16 mg) in CH$_2$Cl$_2$ (1 mL) TFA (1 mL) was added. After 2h the solvent was removed to give the title compound (14 mg).

$^1$H NMR (DMSO-d$_6$/400 MHz) δ ppm: 2.9 (dd, 1H), 3.08 (dd, 1H), 3.95 (m, 1H), 7.25 (s, 1H), 7.38 (s, 1H), 7.90 (2H), 7.94 (d, 2H), 8.64 (d, 2H), 12.38 (s br, 1H).

[M+H]$^+$=471

The following compounds were made by the processes described hereinabove:

6-(Isopropylamino-methyl)-2-pyridin-4-yl-1,5,6,7-tetrahydro-pyrrolo[3,2-c]pyridin-4-one;

6-[(Diisopropylamino)-methyl]-2-pyridin-4-yl-1,5,6,7-tetrahydro-pyrrolo[3,2-c]pyridin-4-one;

6-(3-Amino-propyl)-2-(3-fluoro-pyridin-4-yl)-1,5,6,7-tetrahydro-pyrrolo[3,2-c]pyridin-4-one;

2-(3-Fluoro-pyridin-4-yl)-7-(3,3,3-trifluoro-propyl)-1,5,6,7-tetrahydro-pyrrolo[3,2-c]pyridin-4-one;

7-(2-Fluoro-ethyl)-2-(3-fluoro-pyridin-4-yl)-1,5,6,7-tetrahydro-pyrrolo[3,2-c]pyridin-4-one;

6-Benzyloxymethyl-2-(3-fluoro-pyridin-4-yl)-1,5,6,7-tetrahydro-pyrrolo[3,2-c]pyridin-4-one;

2-(2-Amino-pyrimidin-4-yl)-1-ethyl-7-(2-fluoro-ethyl)-1,5,6,7-tetrahydro-pyrrolo[3,2-c]pyridin-4-one;

2-(2-Amino-pyrimidin-4-yl)-7-(2-fluoro-ethyl)-1-(2,2,2-trifluoro-ethyl)-1,5,6,7-tetrahydro-pyrrolo[3,2-c]pyridin-4-one;

2-(2-Amino-pyrimidin-4-yl)-1-ethyl-7-(3,3,3-trifluoro-propyl)-1,5,6,7-tetrahydro-pyrrolo[3,2-c]pyridin-4-one;

2-(2-Amino-pyrimidin-4-yl)-1-(2,2,2-trifluoro-ethyl)-7-(3,3,3-trifluoro-propyl)-1,5,6,7-tetrahydro-pyrrolo[3,2-c]pyridin-4-one; and 2-(2-Amino-pyrimidin-4-yl)-6-azidomethyl-1,5,6,7-tetrahydro-pyrrolo[3,2-c]pyridin-4-one.

It is to be understood that many modifications and variations may be devised given the above description of the principles of the invention. It is intended that all such modifications and variations can be considered as within the spirit and scope of this invention, as it is defined in the following claims.

We claim:

1. A compound represented by formula (I)

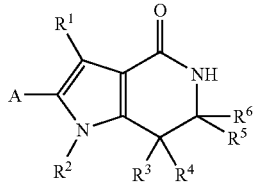

wherein

A is selected from the group consisting of pyridin-4-yl, 3-fluoro-pyridin-4-yl, and 2-amino-pyrimidin-4-yl;

$R^1$ is selected from the group consisting of hydrogen, halogen and ($C_1$-$C_6$)alkyl;

$R^2$ is selected from the group consisting of hydrogen, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)haloalkyl, ($C_1$-$C_6$)polyfluorinated alkyl, heterocyclyl, aryl, heteroaryl, ($C_3$-$C_6$)cycloalkyl-($C_1$-$C_6$)alkyl, heterocyclyl-($C_1$-$C_6$)alkyl, aryl-($C_1$-$C_6$)alkyl, heteroaryl-($C_1$-$C_6$)alkyl, ($C_1$-$C_8$)hydroxyalkyl, ($C_1$-$C_8$)alkoxy-($C_1$-$C_8$)alkyl, aryloxy-($C_1$-$C_8$)alkyl, heteroaryloxy-($C_1$-$C_8$)alkyl, ($C_1$-$C_8$)aminoalkyl, ($C_1$-$C_8$)alkylamino-($C_1$-$C_8$)alkyl, ($C_1$-$C_8$)dialkylamino-($C_1$-$C_8$)alkyl, carbamoyl-($C_1$-$C_8$)alkyl, and alkoxycarbonyl, wherein each of said aryl, heteroaryl, heterocyclyl, aryloxy, and heteroaryloxy moieties can be unsubstituted or substituted by one or more substituents, each substituent being independently selected from the group consisting of alkyl, aryl, —$OCF_3$, —OC(O)alkyl, —OC(O)aryl, —$CF_3$, heteroaryl, aralkyl, alkylaryl, heteroaralkyl, alkylheteroaryl, hydroxy, hydroxyalkyl, alkoxy, aryloxy, aralkoxy, acyl, aryl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, —NH(alkyl), —NH(cycloalkyl), and —N(alkyl)$_2$;

$R^3$, $R^4$, $R^5$ and $R^6$ are each independently selected from the group consisting of hydrogen, ($C_1$-$C_6$)haloalkyl, ($C_1$-$C_6$)polyfluorinated alkyl, ($C_1$-$C_6$)haloalkenyl, ($C_1$-$C_6$) polyfluroinated alkenyl, ($C_1$-$C_8$)hydroxyalkyl, ($C_1$-$C_8$) alkoxy-($C_1$-$C_8$)alkyl, aryloxy-($C_1$-$C_8$)alkyl, heteroaryloxy-($C_1$-$C_8$)alkyl, aryl-($C_1$-$C_8$)alkoxy-($C_1$-$C_8$)alkyl, ($C_1$-$C_8$)azidoalkyl group, ($C_1$-$C_8$)aminoalkyl, ($C_1$-$C_8$)alkylamino-($C_1$-$C_8$)alkyl, ($C_1$-$C_8$)dialkylamino-($C_1$-$C_8$)alkyl, and ($C_1$-$C_8$)alkyl-OC(O)-amino ($C_1$-$C_8$)alkyl, with the proviso that at least one of: $R^3$, $R^4$, $R^5$ or $R^6$ is different from hydrogen;

or a pharmaceutically acceptable salt or solvate thereof.

2. The compound according to claim 1 wherein both $R^3$ and $R^4$ are hydrogen atoms.

3. The compound according to claim 1, wherein both $R^5$ and $R^6$ are hydrogen atoms.

4. The compound according to claim 1 wherein $R^1$, $R^4$, $R^5$ and $R^6$ are hydrogen atoms.

5. The compound according to claim 1 wherein $R^1$, $R^3$, $R^4$ and $R^6$ are hydrogen atoms.

6. A method for treating a cell proliferatve disorder or condition in a mammal comprising administering to a mammal in need of said treatment a compound according to claim 1.

7. The method according to claim 6, wherein said disorder or condition is caused by or is associated with an altered Cdk2 or Cdc7 kinase activity.

8. A pharmaceutical composition comprising an amount of the compound according to claim 1, or a pharmaceutically acceptable salt or solvate thereof, and a pharmaceutically acceptable carrier.

9. A compound according to claim 1 selected from the group consisting of:
(R)-6-benzyloxymethyl-2-pyridin-4-yl-1,5,6,7-tetrahydro-pyrrolo[3,2-c]pyridin-4-one;
DL-7-(2-fluoro-ethyl)-2-pyridin-4-yl-1,5,6,7-tetrahydro-pyrrolo[3,2-c]pyridin-4-one;
(R) and (S)-7-(2-fluoro-ethyl)-2-pyridin-4-yl-1,5,6,7-tetrahydro-pyrrolo[3,2-c]pyridin-4-one hydrochloride;
6-Azidomethyl-2-pyridin-4-yl-1,5,6,7-tetrahydro-pyrrolo[3,2-c]pyridin-4-one;
(R)-2-(2-Amino-pyrimidin-4-yl)-6-benzyloxymethyl-1,5,6,7-tetrahydro-pyrrolo[3,2-c]pyridin-4-one;
DL-2-(2-Amino-pyrimidin-4-yl)-7-(2-benzyloxypropyl)-1,5,6,7-tetrahydro-pyrrolo[3,2-c]pyridin-4-one;
DL-2-(2-amino-pyrimidin-4-yl)-7-(2-fluoro-ethyl)-1,5,6,7-tetrahydro-pyrrolo[3,2-c]pyridin-4-one;
DL-2-(2-amino-pyrimidin-4-yl)-7-(3,3,3-trifluoro-propyl)-1,5,6,7-tetrahydro-pyrrolo[3,2-c]pyridin-4-one hydrochloride;
DL-2-(2-amino-pyrimidin-4-yl)-7-(3, 3-difluoro-allyl)-1,5,6,7-tetrahydro-pyrrolo[3,2-c]pyridin-4-one hydrochloride;
DL-6-(3-amino-propyl)-2-pyridin-4-yl-1,5,6,7-tetrahydro-pyrrolo[3,2-c]pyridin-4-one;
DL-2-(2-amino-pyrimidin-4-yl)-7-(3-hydroxy-propyl)-1,5,6,7-tetrahydro-pyrrolo[3,2-c]pyridin-4-one;
(R)-2-(2-amino-pyrimidin-4-yl)-6-benzytoxymethyl-1-(2,2,2-trifluoro-ethyl)-1,5,6,7-tetrahydro-pyrrolo[3,2-c]pyridin-4-one;
DL-6-hydroxymethyl-2-pyridin-4-yl-1,5,6,7-tetrahydro-pyrrolo[3,2-c]pyridin-4-one hydrochloride;
DL-6-(3-benzylamino-propyl)-2-pyridin-4-yl-1,5,6,7-tetrahydro-pyrrolo[3,2-c]pyridin-4-one and DL-6-(3-dibenzylamino-propyl)-2-pyridin-4-y-1,5,6,7-tetrahydro-pyrrolo[3,2-c]pyridin -4-one;
DL-6-(3-isobutylamino-propyl)-2-pyridin-4-yl-1,5,6,7-tetrahydro-pyrrolo[3,2-c]pyridin -4-one;
DL-6-(3-diisobutylamino-propyl)-2-pyridin-4-yl-1,5,6,7-tetrahydro-pyrrolo[3,2-c]pyridin-4-one; (4-Oxo-2-pyridin-4-yl-4,5,6,7-tetrahydro-1H-pyrrolo[3,2-c]pyridin-6-ylmethyl)-carbamic acid tert-butyl ester;
6-Aminomethyl-2-pyridin-4-yl-1,5,6,7-tetrahydro-pyrrolo[3,2-c]pyridin-4-one bis-trifluoroacetate;
6-(Isopropylamino-methyl)-2-pyridin-4-yl-1,5,6,7-tetrahydro-pyrrolo[3,2-c]pyridin-4-one;
6-[(Diisopropylamino)-methyl]-2-pyridin-4-yl-1,5,6,7-tetrahydro-pyrrolo[3,2-c]pyridin -4-one;
6-(3-Amino-propyl)-2-(3-fluoro-pyridin-4-yl)-1,5,6,7-tetrahydro-pyrrolo[3,2-c]pyridin-4-one;
2-(3-Fluoro-pyridin-4-yl)-7-(3,3,3-trifluoro-propyl)-1,5,6,7-tetrahydro-pyrrolo[3,2-c]pyridin-4-one;
7-(2-Fluoro-ethyl)-2-(3-fluoro-pyridin-4-yl)-1,5,6,7-tetrahydro-pyrrolo[3,2-c]pyridin-4-one;
5-(2-Benzyloxy-ethyl)-piperidine-2,4-dione;
DL-2-(2-amino-pyrimidin-4-yl)-7-(2-hydroxy-ethyl)-1,5,6,7-tetrahydro-pyrrolo[3,2-c]pyridin-4-one;

DL-2-(2-Amino-pyrimidin-4-yl)-7-(2-hydroxy-propyl)-1,5,6,7-tetrahydro-pyrrolo[3,2-c]pyridin-4-one;

6-Benzyloxymethyl-2-(3-fluoro-pyridin-4-yl)-1,5,6,7-tetrahydro-pyrrolo[3,2-c]pyridin-4-one; and 2-(2-Amino-pyrimidin-4-yl)-1-ethyl-7-(2-fluoro-ethyl)-1,5,6,7-tetrahydro-pyrrolo[3,2-c]pyridin-4-one.

* * * * *